(12) United States Patent
Leeflang et al.

(10) Patent No.: US 11,116,938 B2
(45) Date of Patent: *Sep. 14, 2021

(54) ELECTRODE CATHETERS AND METHODS FOR MAKING THEM

(71) Applicant: CLPH, LLC, Palo Alto, CA (US)

(72) Inventors: Stephen A. Leeflang, Sunnyvale, CA (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 16/121,463

(22) Filed: Sep. 4, 2018

(65) Prior Publication Data

US 2018/0369537 A1 Dec. 27, 2018

Related U.S. Application Data

(63) Continuation of application No. 14/738,628, filed on Jun. 12, 2015, now Pat. No. 10,071,222, which is a (Continued)

(51) Int. Cl.
*A61M 25/00* (2006.01)
*A61B 5/00* (2006.01)
(Continued)

(52) U.S. Cl.
CPC ............ *A61M 25/005* (2013.01); *A61B 5/24* (2021.01); *A61B 5/6852* (2013.01);
(Continued)

(58) Field of Classification Search
CPC ............ A61M 25/005; A61M 25/0012; A61M 25/0147; A61M 25/0032;
(Continued)

(56) References Cited

U.S. PATENT DOCUMENTS 5,275,152 A * 1/1994 Krauter ................ A61B 1/0052
138/109
6,213,995 B1 * 4/2001 Steen ..................... A61B 18/14
604/527

(Continued)

*Primary Examiner* — Bhisma Mehta
*Assistant Examiner* — James D Ponton
(74) *Attorney, Agent, or Firm* — William A. English; Vista IP Law Group LLP

(57) ABSTRACT

Catheters, sheaths, or other tubular devices are provided that include a proximal end, a distal end sized for introduction into a patient's body, and a steerable distal portion carrying a plurality of electrodes. The tubular device includes a primary lumen extending between the proximal and distal ends; a steering element lumen adjacent the primary lumen; a plurality of wires extending proximally from the electrodes, and reinforcement members including windings extending helically along at least the distal portion, at least some of the windings passing between the primary and steering element lumens and wires, and at least some of the windings surrounding the primary lumen and one or both of the steering element lumen and the wires. In one embodiment, a steering element is slidably disposed within the auxiliary lumen. Apparatus and methods for making such tubular devices are also provided.

15 Claims, 11 Drawing Sheets

Related U.S. Application Data continuation of application No. PCT/US2015/030043, filed on May 8, 2015, and a continuation-in-part of application No. 14/215,060, filed on Mar. 17, 2014, now Pat. No. 9,427,551.

(60) Provisional application No. 61/990,116, filed on May 8, 2014, provisional application No. 61/802,490, filed on Mar. 16, 2013, provisional application No. 61/917,334, filed on Dec. 17, 2013, provisional application No. 61/930,672, filed on Jan. 23, 2014.

(51) Int. Cl.
| | | |
|---|---|---|
| *A61B 18/14* | (2006.01) | |
| *A61M 25/01* | (2006.01) | |
| *A61M 39/08* | (2006.01) | |
| *A61B 5/24* | (2021.01) | |

(52) U.S. Cl.
CPC ..... *A61B 18/1492* (2013.01); *A61M 25/0012* (2013.01); *A61M 25/0147* (2013.01); *A61M 39/08* (2013.01); *A61M 25/0032* (2013.01); *A61M 2025/0047* (2013.01); *A61M 2025/0059* (2013.01); *A61M 2025/0062* (2013.01); *Y10T 29/49117* (2015.01); *Y10T 29/49826* (2015.01)

(58) Field of Classification Search
CPC .. A61M 2025/0047; A61M 2025/0059; A61M 2025/0062; A61M 39/08; A61B 5/04; A61B 5/6852; A61B 18/1492
See application file for complete search history.

(56) References Cited

U.S. PATENT DOCUMENTS

| | | | |
|---|---|---|---|
| 6,554,820 B1* | 4/2003 | Wendlandt | A61M 25/005 604/527 |
| 2003/0199817 A1* | 10/2003 | Thompson | A61M 25/0147 604/95.01 |
| 2012/0172714 A1* | 7/2012 | Govari | A61M 25/0012 600/424 |
| 2012/0277671 A1* | 11/2012 | Fuentes | A61M 25/005 604/95.04 |

\* cited by examiner

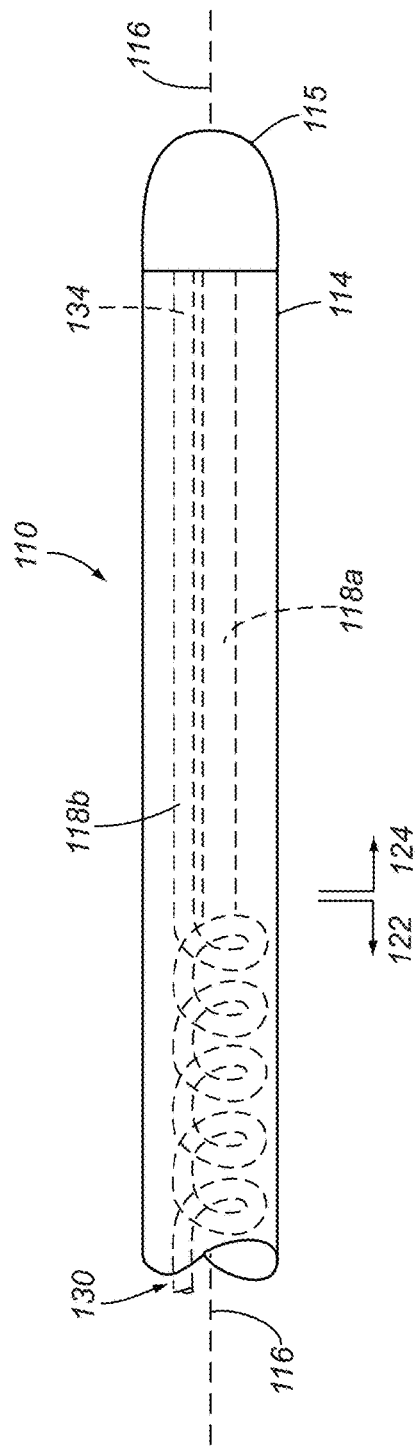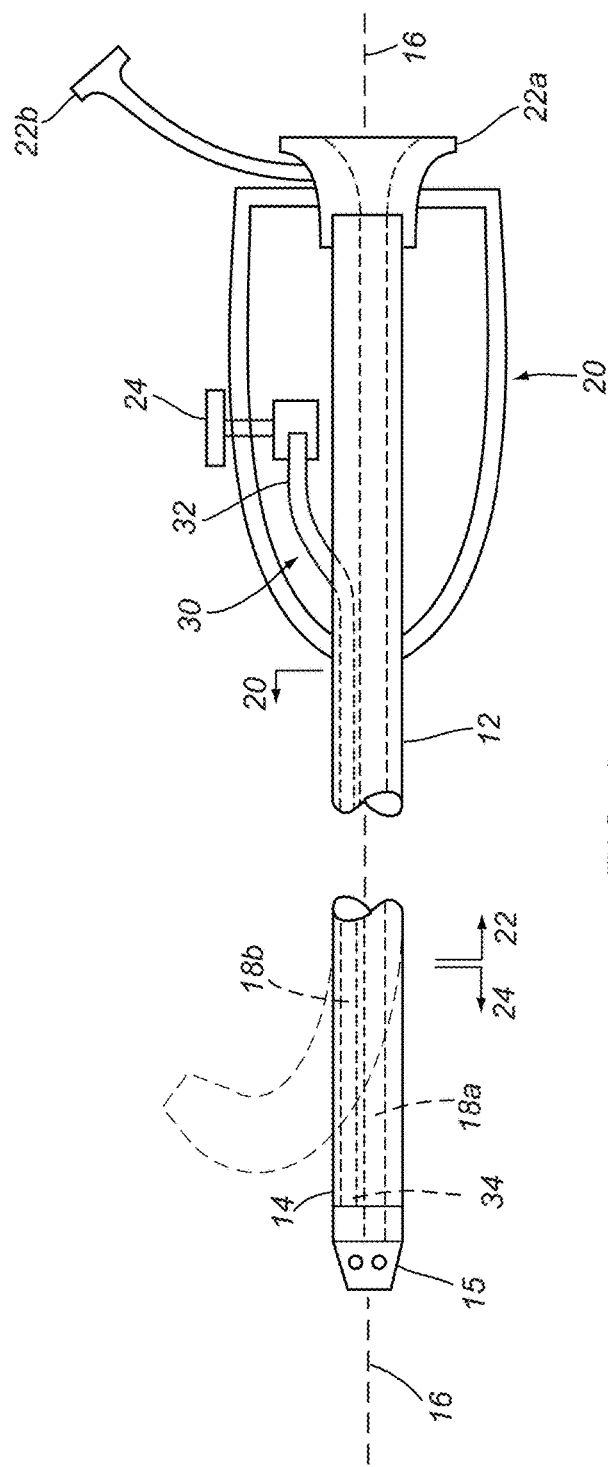
FIG. 2
FIG. 3

ELECTRODE CATHETERS AND METHODS FOR MAKING THEM

RELATED APPLICATION DATA

This application is a continuation of application Ser. No. 14/738,628, filed Jun. 12, 2015, issuing as U.S. Pat. No. 10,071,222, which is a continuation of International application No. PCT/US2015/030043, filed May 8, 2015, which claims benefit of provisional application Ser. No. 61/990,116, filed May 8, 2014, and is a continuation-in-part of application Ser. No. 14/215,060, filed Mar. 17, 2014, now U.S. Pat. No. 9,427,551, which claims benefit of provisional application Ser. No. 61/802,490, filed Mar. 16, 2013, 61/917,334, filed Dec. 17, 2013, and 61/930,672, filed Jan. 23, 2014, the entire disclosures of which are expressly incorporated by reference herein.

FIELD OF THE INVENTION

The present invention relates generally to reinforced catheters, sheaths, or other tubular devices including multiple lumens, and, more particularly, to steerable catheters, sheaths, or other tubular devices including electrodes and/or sensing elements and braided or other reinforcement configurations to enhance support of a steerable portion of the tubular devices, and to methods for making such tubular devices.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or other steering elements may be provided within the catheter, e.g., that are coupled to the distal portion and may be pulled or advanced from the proximal end to deflect the distal portion. For example, a steering element may be provided that is intended to deflect the distal portion within a predetermined plane and/or into a desired curved shape.

Pull wires are a common way to impart deflection ability to such a catheter. However, there are a number of drawbacks associated with such pull wires. For example, a pull wire occupies a significant amount of space within the catheter body. In addition, a pull wire frequently needs to be reinforced, e.g., on the inside and outside of the braid or other reinforcement of the catheter, e.g., to prevent "pull through" when the pull wire is actuated by pushing or pulling, i.e., the resulting bending moment may cause the pull wire to separate layers of or tear at least partially through the wall of catheter, potentially splitting the catheter. Further, a pull wire can make the torque properties of the catheter non-homogenous, making it difficult or impossible to torque the catheter when the pull wire is actuated, e.g., within a tortuous pathway. Further, auxiliary lumens, in particular those located in the wall of a large bore sheath, are difficult to manufacture with consistency due to difficulties with alignment, hand assembly, and the like.

For many applications, such a catheter may include one or more electrodes and/or sensing elements coupled to one or more wires or other conducting elements that extend along at least a portion of the catheter. These components, however, may increase the overall size of the catheter, e.g., to provide a lumen for the wires, given the need for other lumens in the device, e.g., a primary lumen, pull wire lumen(s), and the like. Further, the material of the wire(s) may not easily accommodate bending of the catheter, e.g., when a pull wire is used to steer the catheter during delivery and/or otherwise during a procedure, and/or the wire(s) may modify the deflection profile of the catheter adversely.

Accordingly, there is a need for improved steerable catheters, sheaths, and other tubular devices and methods of their manufacture.

SUMMARY

The present invention is directed to reinforced catheters, sheaths, or other tubular devices including multiple lumens. More particularly, the present invention is directed to steerable catheters, sheaths, or other tubular devices including one or more electrodes and/or sensing elements, conducting elements coupled to such electrodes and/or sensing elements and extending along the tubular device, and/or braided or other reinforcement configurations that enhance support of a steerable portion of the tubular devices, and/or to methods for making such catheters, sheaths, or other tubular devices.

In accordance with one embodiment, a tubular device is provided, e.g., for a catheter or sheath, comprising a proximal end and a distal end sized for introduction into a patient's body. The tubular device may include a central lumen extending between the proximal and distal ends; one or more elongate conducting elements extending at least partially between the proximal and distal ends adjacent the central lumen; and one or more reinforcement members including windings extending helically around the central lumen between the proximal and distal ends. At least some of the windings may pass between the central lumen and the conducting element(s) and at least some of the windings surrounding both the central lumen and the conducting element(s). In addition, one or more layers may surround the one or more reinforcement members and one or more electrodes or sensing elements may be provided on the distal end coupled to the conducting element(s).

In accordance with another embodiment, an apparatus is provided for performing a procedure within a patient's body that includes a tubular member including a proximal end, a distal end sized for introduction into a patient's body, a central axis extending therebetween, and a distal portion extending distally from an intermediate portion to the distal end; a primary lumen extending between the proximal and distal ends and aligned with and/or otherwise surrounding the central axis; a steering element lumen adjacent the primary lumen and offset from the central axis; one or more conducting elements extending at least partially along the distal portion adjacent the primary lumen, and one or more reinforcement members including windings extending helically along at least the distal portion. At least some of the windings pass between the primary lumen and the steering element lumens, at least some of the windings pass between the primary lumen and the one or more conducting element, and at least some of the windings surround the primary lumen and one or both of the steering element lumen and the one or more conducting elements. A steering element may be slidably disposed within the steering element lumen and may include a distal end fixed to the tubular member distal end and a proximal end coupled to an actuator on the tubular member proximal end such that, actuation of the actuator applies axial tension or compression to the steering element, thereby causing the distal portion to bend.

In accordance with still another embodiment, an apparatus is provided for performing a procedure within a patient's body that includes a tubular member including a proximal end, a distal end sized for introduction into a patient's body, a central axis extending therebetween, and a distal portion extending distally from an intermediate portion to the distal end. A primary lumen extends between the proximal and distal ends and aligned with and/or otherwise surrounding the central axis, an auxiliary lumen and one or more wires or other conducting elements are disposed adjacent the primary lumen and offset from the central axis, the auxiliary lumen and conducting elements extending substantially parallel to the primary lumen along the distal portion. One or more reinforcement members may include windings extending helically along at least the distal portion, at least some of the windings passing between the primary lumen and one or both of the auxiliary lumen and the conducting elements lumens, and at least some of the windings surrounding both the primary and auxiliary lumens and the conducting elements.

In one embodiment, the apparatus further includes a steering element slidably disposed within the auxiliary lumen and including a distal end fixed to the tubular member distal end and a proximal end adjacent the proximal end of the tubular member; and an actuator on the proximal end coupled to the steering element proximal end such that, actuation of the actuator applies axial tension or compression to the steering element, thereby causing the distal portion to bend.

In addition, the apparatus may also include one or more electrodes and/or sensing elements on the distal portion that are coupled to the one or more conducting elements. For example, the conducting elements may include a plurality of wires extending along the distal portion that are coupled to a plurality of electrodes spaced apart from one another on the distal portion. The wires may extend along the distal portion in a non-linear path to accommodate bending of the distal portion, e.g., when the steering element is actuated. For example, the wires may extend adjacent one another in a generally sinusoidal or other curvilinear path adjacent the primary lumen, or may extend helically around the primary lumen.

In accordance with yet another embodiment, a method is provided for making a tubular body that includes directing a primary mandrel along a central axis of a braiding apparatus such that the primary mandrel is surrounded by a plurality of reinforcement carrying elements; and directing one or more conducting elements adjacent to the primary mandrel. One or more reinforcement members from the reinforcement carrying elements may be wrapped helically around the primary mandrel such that some windings of the one or more reinforcement members surround the primary mandrel and pass between the primary mandrel and the one or more conducting elements, and some windings of the one or more reinforcement members surround both the primary mandrel and the one or more conducting elements. An outer jacket may be applied around the primary mandrel and the one or more conducting elements after wrapping the one or more reinforcement members therearound. The primary mandrel may be removed to define a primary lumen within the tubular body.

One or more electrodes and/or sensing elements may be mounted on the distal portion, which may be electrically coupled to the one or more conducting elements. For example, the conducting elements may include a plurality of wires and the wires may be exposed at desired regions of the distal portion, and spot electrodes may be applied on the distal portion at the desired regions and coupled to the wires.

In addition, the method may also include directing a secondary mandrel adjacent to the primary mandrel and offset from the central axis. When the reinforcement members are wrapped around the assembly, at least some windings may pass between the primary mandrel and the secondary mandrel, and some windings of the one or more reinforcement members surround both the primary mandrel and the secondary mandrel. The secondary mandrel may later be removed to define an auxiliary lumen within the tubular body adjacent the primary lumen, and a pull wire may be introduced into the auxiliary lumen and coupled to the distal end.

In accordance with still another embodiment, a method is provided for making a tubular body that includes directing a primary mandrel along a central axis of a braiding apparatus such that the primary mandrel is surrounded by a plurality of reinforcement carrying elements; and directing one or more conducting element adjacent to the primary mandrel. One or more reinforcement members may be wrapped from the reinforcement carrying elements helically around the primary mandrel such that some windings of the one or more reinforcement members surround the primary mandrel and pass between the primary mandrel and the one or more conducting elements and some windings of the one or more reinforcement members surround both the primary mandrel and the one or more conducting elements. Optionally, the reinforcement carrying elements may be rotated relative to the primary mandrel while wrapping the one or more reinforcement members around the primary mandrel, thereby wrapping the one or more conducting elements helically around at least a portion of the primary mandrel.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2 is a cross-sectional view of another embodiment of a catheter including a steering lumen extending helically along an intermediate portion of the catheter and axially along a distal portion of the catheter to provide a steerable distal portion.

FIG. 3 is a cross-sectional view of a catheter including a handle on a proximal end of the catheter and a steering element within an auxiliary lumen of the catheter that exits the auxiliary lumen within the handle and is coupled to an actuator on the handle.

DETAILED DESCRIPTION OF THE EXEMPLARY EMBODIMENTS

Figure 1A:
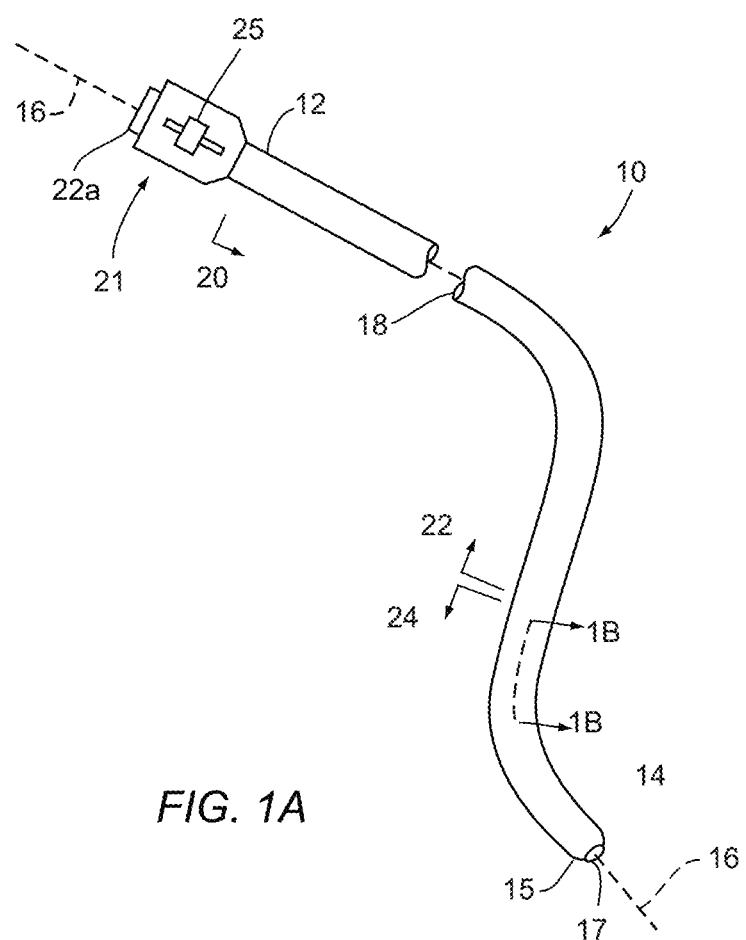
FIG. 1A is a perspective view of an exemplary embodiment of a catheter, including multiple lumens extending between proximal and distal ends thereof, and including a steerable distal portion.
Figure 1B:
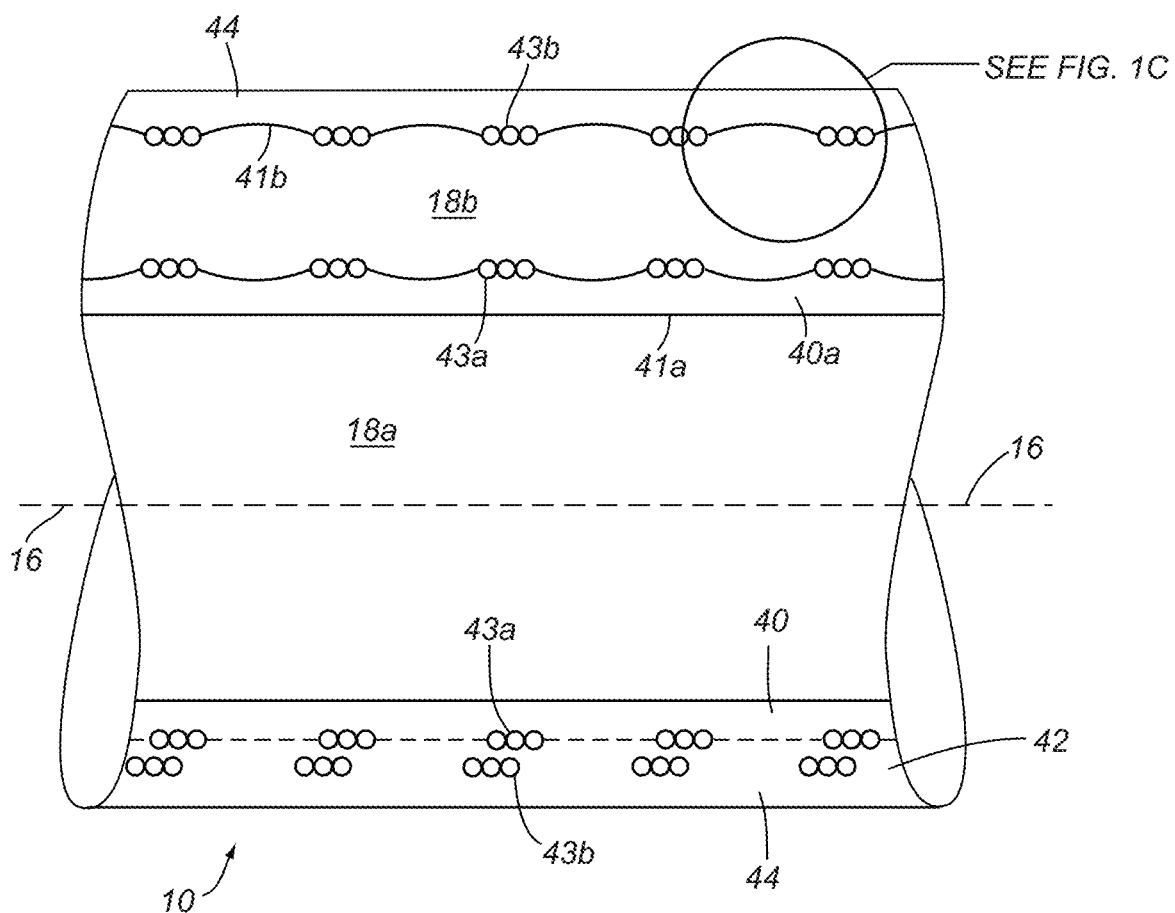
FIG. 1B is a cross-sectional view of the catheter of FIG. 1A, taken along line 1B-1B, showing reinforcement members positioned around primary and auxiliary lumens of the catheter.

Turning to the drawings, FIGS. 1A and 1B show an exemplary embodiment of an apparatus 10 for introduction into a body lumen (not shown), e.g., for performing a diagnostic and/or therapeutic procedure within a patient's body. In exemplary embodiments, the apparatus 10 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown). In exemplary embodiments, the apparatus 10 may have a length between about ten and one hundred ten centimeters (10-110 cm), and an outer diameter between about four and ten French (4-24 Fr).

Generally, the apparatus 10 is an elongate tubular member including a proximal end 12, a distal end 14 sized for insertion into a body lumen, a central longitudinal axis 16 extending between the proximal and distal ends 12, 14, and one or more lumens 18 extending between the proximal and distal ends 12, 14. For example, as shown in FIG. 1B, the apparatus 10 may include a central or primary lumen 18a, e.g., sized for receiving or carrying one or more instruments or other elements (not shown) therethrough. In exemplary embodiments, the central lumen 18a may be sized for receiving or carrying a guide wire, procedure catheter, balloon catheter, ablation catheter, cardiac lead, needle, or other instrument (not shown), one or more wires or other conductors, one or more optical fibers, one or more tubes or accessory lumens, one or more mechanical elements, one or more sensors, and/or sized for delivering and/or removing fluids or other flowable agents or materials therethrough.

In one embodiment, shown in FIG. 1A, the central lumen 18a may exit at or communicate with an outlet 17 in the distal end 14, e.g., to allow a guidewire or other instrument (not shown) to pass therethrough and/or for delivering or aspirating fluid therethrough. In an alternative embodiment, such as the apparatus 110 shown in FIG. 2, the central lumen 118a may be enclosed, e.g., terminating within or adjacent the distal end 114, e.g., to isolate the central lumen 118a and/or elements carried therein from the environment outside the apparatus 110. In an exemplary embodiment where the apparatus 110 is an ablation and/or mapping catheter, the central lumen 118a may carry one or more wires or other conductors, thermocouple wires, tubes, and the like (not shown), e.g., coupled to electrodes or other elements (also not shown) carried on the distal end 114.

Returning to FIG. 1B, in addition to the central lumen 18a, an auxiliary lumen 18b may be provided, e.g., extending adjacent the central lumen 18a, e.g., substantially parallel to and radially offset relative to the central axis 16. In an exemplary embodiment, the auxiliary lumen 18b may be a steering element lumen configured to receive a pull wire or other steering element (not shown, see, e.g., the steering element 30 shown in FIG. 3) therein, e.g., to bend or otherwise deflect a distal portion 24 of the apparatus 10, as described further below. Optionally, the apparatus 10 may include one or more additional lumens (not shown), e.g., one or more additional steering element lumens, inflation lumens (e.g., if the apparatus 10 includes one or more balloons, not shown on the distal end 14), and/or accessory lumens.

Figure 5A:
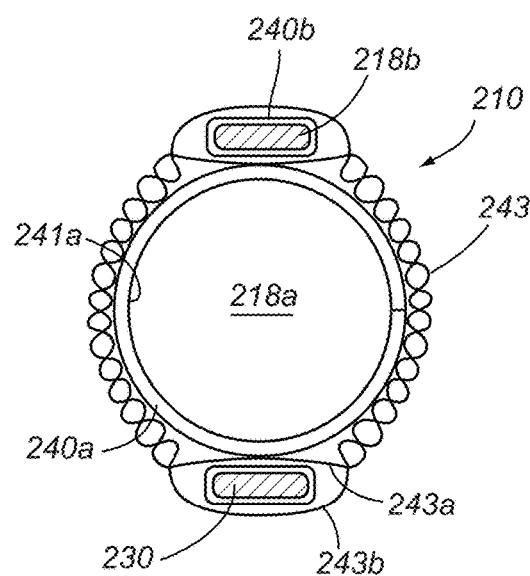
FIGS. 5A and 5B are cross-sections of alternative embodiments of steerable catheters including multiple auxiliary lumens and steering elements.

For example, as shown in FIG. 5A, an apparatus 210 is shown that may be generally similar to the apparatus 10, e.g., including a central lumen 218a surrounded by an inner liner 240a and one or more reinforcement members 243. Unlike the apparatus 10, the apparatus 210 includes two auxiliary lumens 218b, each surrounded by a liner 240b and having a steering element 230 therein. Similar to the apparatus 10, the reinforcement members 243 include some windings 243a that pass between the central and auxiliary lumens 218a, 218b and some windings 243b that surround all of the lumens 218. In a further alternative shown in FIG. 5B, an apparatus 210' is shown that includes four auxiliary lumens 218b' with steering elements 230' therein.

Figure 5B:
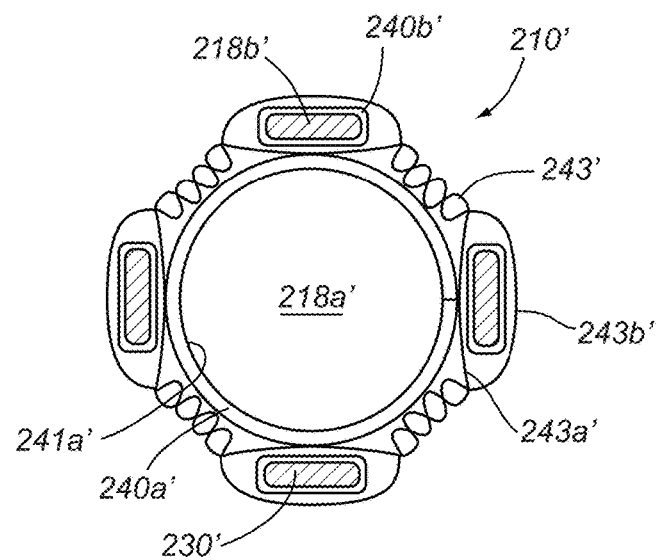
Figure 6A:
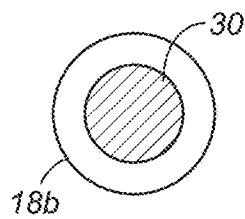
FIGS. 6A-6G are details showing alternative cross-sections of auxiliary lumens and steering elements that may be included in the tubular devices herein.
Figure 6B:
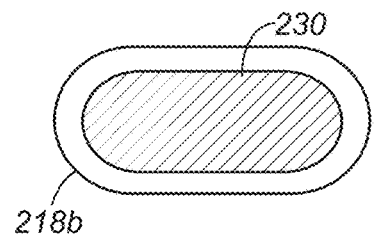

Turning to FIGS. 6A-6G, the auxiliary lumens may have a variety of cross-sectional shapes. For example, FIG. 6A shows a substantially circular auxiliary lumen 18b with a slightly smaller substantially circular steering element 30 disposed therein, e.g., similar to the apparatus 10 shown in FIGS. 1 and 3. In another embodiment, shown in FIG. 6B, the auxiliary lumen 218b has an elliptical or oval shape including a similarly shaped steering element 230 therein, e.g., similar to the apparatus 210, 210' shown in FIGS. 5A and 5B. An oval shape may reduce an outer profile of the apparatus 210, e.g., compared to the circular lumen 18b of FIG. 6A, and/or may provide a desired bending moment on a distal portion (not shown) of the apparatus 210 when actuated.

Figure 6C:
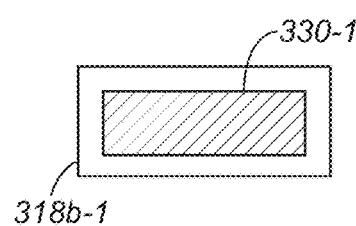
Figure 6D:
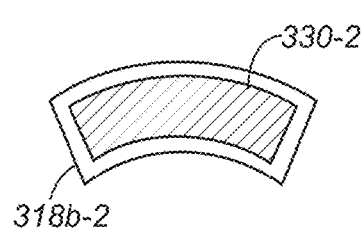
Figure 6E:
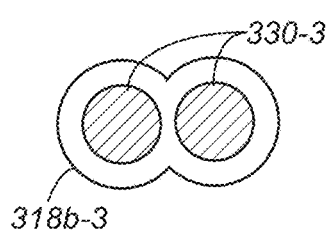

It will be appreciated that other cross-sections may also be provided. For example, FIG. 6C shows a substantially rectangular auxiliary lumen 318b-1 including a similarly shaped steering element 330-1 therein. FIG. 6D shows a curved auxiliary lumen 318*b*-1 including a similarly shaped steering element 330-2, which may define a radius of curvature corresponding to the outer circumference or other shape of the catheter, e.g., which may reduce an overall profile of the catheter (not shown). FIG. 6E shows an auxiliary lumen 318*b*-3 defined by a pair of overlapping circles, which may receive a pair of substantially circular steering elements 330-3 or a single similarly shaped steering element (not shown).

Figure 6F:
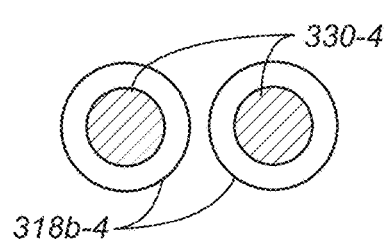

FIG. 6F shows a pair of substantially circular auxiliary lumens 318*b*-4 that may be located immediately adjacent one another and may receive respective substantially circular steering elements 330-4. The steering elements 330-4 may be actuated independently or simultaneously e.g., depending on the actuator configuration on the handle of the catheter (not shown).

Figure 6G:
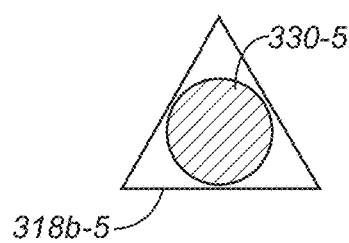

Finally, FIG. 6G shows a triangular auxiliary lumen 318*b*-5 that includes a substantially circular steering element 330-5 therein. Such a configuration may reduce friction between the steering element 330-5 and the wall of the auxiliary lumen 318*b*-5 since the different shapes minimize contact with one another.

Figure 7:
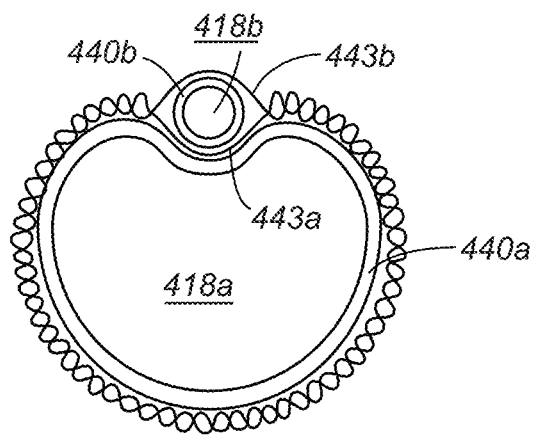
FIG. 7 is a cross-section of another embodiment of a tubular device including a non-circular central lumen and an auxiliary lumen nested at least partially adjacent the central lumen.

As shown in FIGS. 5A and 5B, the primary lumen 218*a*, 218*a*' may have a substantially circular shape. Alternatively, the primary lumen may have other shapes and/or cross-sections. For example, as shown in FIG. 7, the primary lumen 418*a* may have a non-circular shape, e.g., a rounded kidney shape, and the auxiliary lumen 418*b* may be nested partially adjacent the primary lumen 418*a*. The non-circular shape may facilitate introducing instruments through the primary lumen 418*a* with reduced friction, since a rounded or otherwise shaped instrument may have reduced surface contact with the inner surface of the primary lumen 418*a*. In addition, the non-circular primary lumen 418*a* shown in FIG. 7 may facilitate introduction of a compressible or otherwise deformable instrument or device therethrough, since the device may conform at least partially to the non-circular shape of the primary lumen 418*a*. The non-circular primary lumen 418*a* may provide a maximum cross-sectional area for the primary lumen 418*a* while minimizing an overall profile of the catheter, e.g., compared to a circular primary lumen, e.g., due to the additional area provided on either side of the nested auxiliary lumen 418*b*.

Returning to FIG. 1A, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 10. Further, in addition or alternatively, the distal end 14 may include one or more features to enhance radiopacity and/or visibility under ultrasound, MRI or other imaging modalities, e.g., by mounting one or more platinum elements on the distal end 14, doping one or more regions of the distal end 14 with tungsten or barium sulfate, and/or other methods known in the art.

Optionally, as shown in FIG. 1A, the proximal end 12 may include a handle or hub 21, e.g., configured and/or sized for holding and/or manipulating the apparatus 10 from the proximal end 12. In addition, the handle 21 may include one or more ports, e.g., port 22*a* communicating with the central lumen 18*a*, or other respective lumens (not shown). Optionally, the port 22*a* may include one or more valves, e.g., a hemostatic valve (also not shown), which may provide a substantially fluid-tight seal, while accommodating insertion of one or more instruments or fluids into the central lumen 18*a*. In addition or alternatively, a side port 22*b* may be provided on the handle 21, e.g., as shown in FIG. 3, e.g., for delivering fluid into and/or aspirating fluid from the primary lumen 18*a*, e.g., around an instrument inserted into the primary lumen 18*a*. Optionally, the handle 21 and/or proximal end 12 may include one or more connectors, such as luer lock connectors, electrical connectors, and the like, for connecting other devices (not shown) to the apparatus 10, such as syringes, displays, controllers, and the like (also not shown).

In addition, the handle 21 may include one or more actuators, such as sliders, buttons, switches, rotational actuators, and the like, e.g., for activating and/or manipulating components (also not shown) on the distal end 14 or otherwise operating the apparatus 10. For example, as shown in FIGS. 1A and 3, an actuator 25 may be provided that is coupled to a proximal end 32 of the steering element 30 (shown in FIG. 3) within the auxiliary lumen 18*b*, as described further below.

Generally, with particular reference to FIG. 1B, the apparatus 10 may include an inner liner 40, e.g., at least partially or entirely surrounding or otherwise defining the central lumen 18*a*, a reinforcement layer 42 surrounding the inner liner 40, and an outer jacket 44 surrounding the reinforcement layer 42, each of which may extend at least partially between the proximal and distal ends 12, 14 of the apparatus 10. The reinforcement layer 42 and/or outer jacket 44 may be attached to the inner liner 40, e.g., by laminating, adhering, adhesive bonding, ultrasonic welding, reflowing or other heating, and the like, as described elsewhere herein.

In an exemplary embodiment, the central lumen 18*a* is defined by an inner liner 40*a* including an inner surface 41*a*. The inner liner 40*a* may be formed from lubricious material, e.g., PTFE, to provide a lubricious inner surface 41*a*. Alternatively, the inner liner 40 may be formed from one or more layers of thermoplastic or other polymeric material including one or more coatings on the inner surface 41*a* having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Figure 1C:
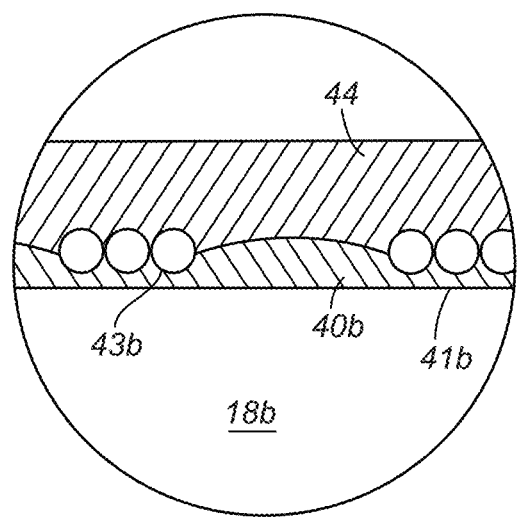
FIG. 1C is a detail of the catheter wall of FIG. 1B, showing reinforcement members and an optional liner that surrounds at least a portion of the auxiliary lumen.

Optionally, as shown in FIG. 1C, an inner liner 40*b* may also at least partially surround the auxiliary lumen 18*b*, which may be formed from a lubricious material and/or may include one or more coatings on its inner surface 41*b*, similar to the inner liner 40*a*. The inner surface 41*b* of the auxiliary lumen 18*b* may have a substantially uniform cross-section, as shown in FIG. 1C. Alternatively, the inner surface 41*b* of the auxiliary lumen 18*b* may have a textured or other variable cross-section along, e.g., along its length and/or about its circumference.

For example, as shown in FIG. 1B, the auxiliary lumen 18*b* may have a narrower cross-section coextensive with the reinforcement members 43*a* and a wider cross-section between the reinforcement members 43*a*. Thus, in this embodiment, a steering element (not shown) slidably inserted into the auxiliary lumen 18*b* may contact the narrower regions and pass freely within the wider regions. Such a variable cross-section may be achieved by controlling one or more parameters during manufacturing, as described further elsewhere herein.

Optionally, any or all of the inner liner 40*a*, reinforcement layer 42, and/or outer jacket 44 may be formed from multiple layers of like or different materials (not shown), e.g., to provide desired material properties in the different portions of the apparatus 10. In an exemplary embodiment, the outer jacket 44 may be formed from PEBAX, nylon, urethane, and/or other thermoplastic material, e.g., such that the material of the outer jacket 44 may be heated and reflowed and/or otherwise formed around the components defining the lumens 18, e.g., as described elsewhere herein.

In one embodiment, one or more of the layers of the apparatus 10 may have a substantially homogenous construction between the proximal and distal ends 12, 14. Alternatively, the construction may vary along the length of the apparatus 10 to provide desired properties, e.g., between proximal, intermediate, and distal portions 20, 22, 24. For example, a proximal portion 20 of the apparatus 10 adjacent the proximal end 12 may be substantially rigid or semi-rigid, e.g., providing sufficient column strength to allow the distal end 14 of the apparatus 10 to be pushed or otherwise manipulated from the proximal end 12, while the distal portion 24 may be substantially flexible. As described further below, the distal portion 24 of the apparatus 10 may be steerable, i.e., may be bent, curved, or otherwise deflected substantially within a steering plane, as described further below.

Returning to FIG. 1B, the reinforcement layer 42 may include one or more reinforcing members, e.g., wound in a braided or other helical configuration around the inner liner 40a, and the outer jacket 44 may include one or more tubular layers surrounding the reinforcement layer 42 and/or between the reinforcement layer 42 and the inner liner 40a. In an exemplary embodiment, the reinforcement layer 42 may include one or more, or a plurality of, round or flat (e.g., rectangular, elliptical, or flat oval) wires, filaments, strands, or other reinforcement members 43, e.g., formed from metal, such as stainless steel, plastic, glass, woven or twisted fibers, such as aramid, and the like, or composite materials.

In one embodiment, a plurality of reinforcement members 43 may be braided around the inner liner 40a, e.g., with each reinforcement member 43 having the same material and/or shape. Alternatively, the reinforcement members 43 may have different sizes and/or shapes, e.g., a first size or shape extending helically in a first direction and a second size or shape (different than the first) extending helically in a second direction (e.g., opposite the first direction).

The reinforcement layer 42 may be configured to substantially transfer torsional forces between the proximal and distal ends 12, 14, e.g., to allow the apparatus 10 to be twisted from the proximal end 12 to rotate the distal end 14 about the longitudinal axis 16 within a patient's body. In addition, the reinforcement layer 42 may allow the distal end 14 of the apparatus 10 to be advanced or otherwise manipulated within a patient's body from the proximal end 12 without substantial risk of buckling and/or kinking. The pitch of the reinforcement layer 42 may be varied along the length of the apparatus 10, e.g., in order to optimize mechanical properties of various segments or portions of the apparatus 10.

In the exemplary embodiment shown in FIG. 1B, the reinforcement members 43 may be applied around the central lumen 18a such that a first set of the reinforcement members 43a including windings that pass between the central lumen 18a and the auxiliary lumen 18b when wrapped around the central lumen 18a, and a second set of reinforcement members including windings 43b that surround both the central lumen 18a and the auxiliary lumen 18b. Stated differently, windings of the first set of reinforcement members 43a may be wrapped around the inner layer 40 surrounding the central lumen 18a without being wrapped around or surrounding the auxiliary lumen 18b, while windings of the second set of reinforcement members 43b are wrapped around and surround both the central lumen 18a and the auxiliary lumen 18b, i.e., including regions disposed between the auxiliary lumen 18b and an outer surface of the apparatus 10, as shown in FIG. 1B.

In an exemplary embodiment, the auxiliary lumen 18b may be radially offset from the central axis 16 substantially along the length of the apparatus 10, e.g., entirely from the distal end 14 to the proximal end 12, thereby offset from a center of mass of the apparatus 10 along its length. In this embodiment, the non-steerable portions of the apparatus 10 may be constructed to resist bending, e.g., having a substantially greater stiffness than the distal portion 24, such that any bending moment generated by a pull wire is applied primarily to the distal portion 24.

Alternatively, the intermediate and/or proximal portions 22, 20 may be constructed to offset the center of mass from the central axis 16, e.g., to align the center of mass with the auxiliary lumen 18b within the intermediate and/or proximal portions 22, 20 (not shown). For example, the apparatus 10 may have a non-circular or other asymmetrical cross-section that minimizes applying a bending moment to the intermediate and/or proximal portions 22, 20, thereby applying any bending moment substantially only to the distal portion 24.

In another embodiment, shown in FIG. 2, an apparatus 110 may be provided that includes an auxiliary or steering lumen 118b that extends helically around an intermediate portion 122 of the apparatus 110 to the proximal portion 120 (or optionally around the proximal portion 120 back to the proximal end 12 of the apparatus 110). As shown, the auxiliary lumen 118b extends axially along a distal portion 124 while offset radially from the central axis 116 of the apparatus 110, e.g., terminating adjacent a distal tip 115 of the apparatus.

A steering element 130 may be slidably received within the auxiliary lumen 118b with a distal end 134 coupled to the distal tip 115 or other structure on the distal end 114. Due to the helical configuration of the auxiliary lumen 118b in the intermediate portion 122, an axial force on the steering element 130 (e.g., due to pulling or pushing on the steering element) may not apply a substantial bending moment on the intermediate portion 122. However, because the auxiliary lumen 118b is offset radially from the central axis 116 of the apparatus 110 along the distal portion 124, an axial force applied to the steering element 130 applies a bending moment to the distal portion 124, thereby causing the distal portion 124 to curve or otherwise bend. More generally, the path of the auxiliary lumen 118b may be varied along the length of the apparatus 110, e.g., to control where a bending moment is applied and/or generate a complex curve in one or more segments of the apparatus 110.

In an alternative embodiment, the auxiliary or steering element lumen may be aligned with the central axis of the apparatus within the intermediate portion (not shown) and offset radially from the central axis within the distal portion. For example, the distal portion may be formed from a tubular body constructed similar to that shown in FIG. 1B, while the intermediate and/or proximal portions may be formed with the auxiliary lumen aligned with the central axis and/or center of mass of the apparatus (not shown).

With additional reference to FIGS. 1A and 3, if the distal portion 24 of the apparatus 10 is steerable, one or more pull wires, cables, fibers, threads, filaments, or other steering elements, such as pull wire 30 shown in FIG. 3 may be slidably received within the auxiliary lumen 18b. The pull wire 30 generally includes a proximal end 32 coupled to the actuator 25 on the handle 21 and extends through the intermediate portion 22 and into the distal portion 24. A distal end 34 of the steering element 30 may be fixed or otherwise coupled to the distal end 14, e.g., to a component defining or adjacent the distal tip 15, as shown in FIG. 3. The steering element 30 may be formed from materials capable of substantially transferring any axial forces applied at the proximal end 32 to the distal end 34, as is known in the art. Optionally, the steering element 30 may include a coating, e.g., PTFE, parylene, silicone, or other lubricious material, an outer sleeve, e.g., formed from HDPE, PTFE, and the like, to reduce friction between the steering element 30 and the wall of the auxiliary lumen 18b. Alternatively or in addition, the inner surface 41b of the auxiliary lumen 18b may be formed from lubricious material and/or may include one or more coatings, as described elsewhere herein. Alternatively or in addition, the auxiliary lumen 18b may include one or more incompressible elements, e.g., a tightly wound coil therearound, e.g., to prevent compression, which may otherwise lead to creating a bending moment along at least part of its length.

During use, the actuator 25 may be activated, e.g., directed proximally or distally relative to the handle 21 and/or the proximal end 12, to apply an axial force to the steering element 30, e.g., tension (when the steering element 30 is pulled) or compression (when the steering element 30 is advanced). Because the steering element 30 is slidable within the auxiliary lumen 18b, the axial force is translated and applied to the distal end 34 coupled to the distal end 14. Because the auxiliary lumen 18b is offset from the central axis 16 along at least the distal portion 24, the axial force applies a bending moment, thereby causing the distal portion to curve or otherwise bend in a desired plane or other manner, e.g., as shown in phantom in FIG. 3. As explained elsewhere herein, the proximal and intermediate portions 20, 22 of the apparatus 10 may be constructed to prevent or minimize bending forces caused by actuation of the steering element 30.

With additional reference to FIG. 1B, the bending moment caused by the steering element 30 within the auxiliary lumen 18b of the distal portion 24 applies radial forces against the wall of the auxiliary lumen 18b. For example, when a proximal force is applied, e.g., to cause the distal portion 24 to bend as shown in phantom in FIG. 3, the steering element 30 may apply an outward force against the inner surface 41b of the auxiliary lumen 18b, i.e., away from the central lumen 18a. Because at least some of the windings 43b (e.g., half) of the reinforcement layer 42 surround the auxiliary lumen 18b, the windings 43b may support the wall of the auxiliary lumen 18b and the adjacent outer jacket 44, thereby reducing the risk of tearing or otherwise damaging the material outside the auxiliary lumen 18b. Conversely, when a distal force is applied, e.g., to cause the distal portion to bend opposite to that shown in phantom in FIG. 3, the steering element 30 may apply an inward force against the inner surface 41b of the auxiliary lumen 41b, i.e., towards the central lumen 18a. Again because at least some of the windings 43a (e.g., half) surround the central lumen 18a, passing between the central and auxiliary lumens 18a, 18b, the windings 43a may support the wall of the auxiliary lumen 18b and the inner liner 40a surrounding the central lumen 18a, thereby reducing the risk of tearing or otherwise damaging the material outside the auxiliary lumen 18b, e.g., tearing into the central lumen 18a. Additionally, when a rotational force is applied to the apparatus 10 while its distal portion 24 is being caused to bend, the steering element 30 may apply at least some component of lateral force within the wall of the apparatus 10, which alone or in combination with the inward and/or outward force described above, may tend to separate the adjacent layers of the apparatus 10, but for the surrounding windings 43a and 43b that reinforce the auxiliary lumen 18b on all sides.

By comparison, catheters that wrap reinforcement members only around both lumens may risk tearing and/or separation, e.g., when a distal force is applied to the steering element. Likewise, catheters that wrap reinforcement members only around a central lumen and then add an outer steering lumen may risk tearing and/or separation, e.g., when a proximal force is applied to the steering element, and/or may increase the profile of the resulting catheter.

With continued reference to FIG. 1B, wrapping some windings 43b of the reinforcement members 43b around both lumens 18a, 18b and some windings 43a just around the central lumen 18a may reduce an overall cross-section of the apparatus 10. For example, additional reinforcement members that may otherwise be added to support a steering element lumen may be eliminated since the windings 43a, 43b automatically support the apparatus 10 on all sides of the auxiliary lumen 18b.

In addition, this configuration of reinforcement members may also enhance torque transmission properties of the apparatus 10. For example, in the embodiment shown in FIG. 2, the auxiliary lumen 118b may be wound helically around the central lumen 118a. When the proximal end (not shown) of the apparatus 110 is rotated to torque the distal portion 124, the helical region of the auxiliary lumen 118b may enhance translation of the torque to the distal portion 124. In general, it may be sufficient to have one to three rotations of the auxiliary lumen 118b in the intermediate region per one hundred eight degrees (180°) of tortuosity.

Figure 4A:
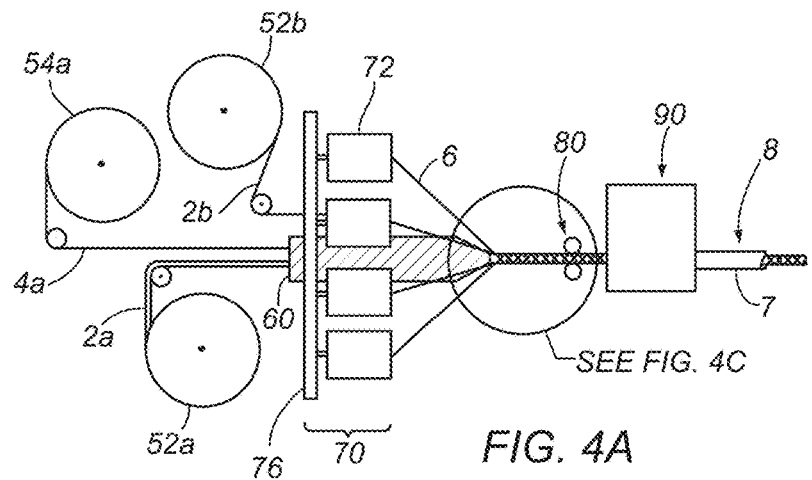
FIG. 4A is a schematic of an exemplary embodiment of an apparatus for making a reinforced tubular member including multiple lumens supported by reinforcement members.
Figure 4B:
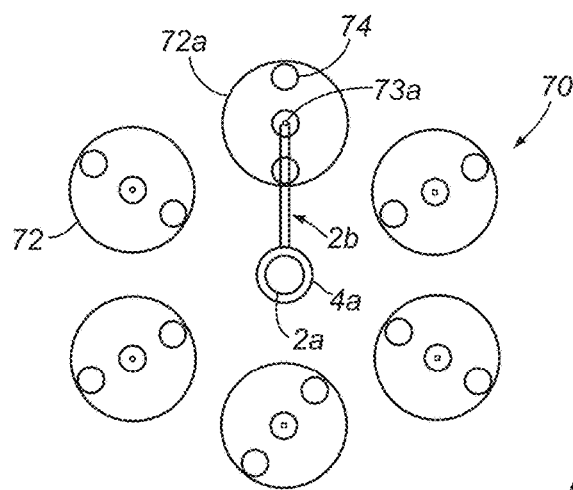
FIG. 4B is a front view of an arrangement of horn gears for creating a braided configuration of reinforcement members that may be included in the apparatus of FIG. 4A.
Figure 4C:
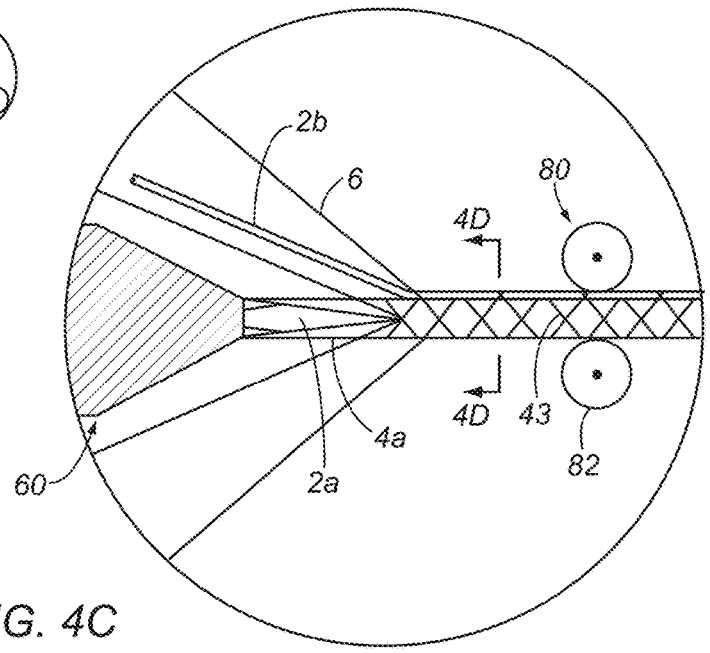
FIG. 4C is a detail showing reinforcement members being braided around a primary mandrel and an auxiliary mandrel for defining lumens of the tubular member.

Turning to FIGS. 4A-4C, various methods may be used for manufacturing and/or assembling any of the embodiments described herein. For example, FIG. 4A shows an exemplary embodiment of an apparatus 50 for making one or more tubular bodies, such as catheters and/or components for catheters, sheaths, or other tubular devices 8. Generally, the apparatus 50 includes a plurality of sources 52, 54 of mandrels 2 and/or liners 4, a guide 60, a source 70 of reinforcement members 6, a drive mechanism 80, and, optionally, a source 90 of jacket material 7.

The apparatus 50 may allow for substantially continuous fabrication of tubular bodies, e.g., wrapping a liner material 4a around a primary mandrel 2a (or the primary mandrel 2a may include a tubular or other liner material provided around it on the source 52, e.g., similar to the liners disclosed in the references incorporated by reference elsewhere herein), positioning an auxiliary mandrel 2b (with optional liner material) adjacent the primary mandrel 2a, braiding a plurality of reinforcement members 4 around the mandrels 2, and optionally, applying outer jacket material 7 around the reinforced mandrels, as described further below.

As used herein, "substantially continuous" means that the apparatus 50 and/or method may operate indefinitely, i.e., to make as few as one or as many as hundreds or thousands of tubular bodies 8, e.g., by substantially simultaneously feeding components of the tubular bodies 8 from sources 52, such as reels, through components of the apparatus 50 until the sources 52 are depleted, whereupon new source(s) may be loaded onto the apparatus 50 and the process continued. Alternatively, the apparatus 50 may be used to create discrete lengths of tubular devices, e.g., if the mandrels and/or liners are provided in specific lengths corresponding to one or more individual tubular devices (not shown). In a further alternative, some of the operations may be performed substantially continuously, while other operations are performed on components intended for one or more individual tubular devices.

Thus, the apparatus 50 and methods herein may be used to make one or more relatively long tubular bodies 8, e.g., that are substantially longer than finished catheters or other tubular devices. For example, one resulting tubular body 8 may be collected, e.g., on a take-up reel or container (not shown), or may be separated into individual shorter tubular bodies, e.g., using a cutter or other tool (not shown), that may be incorporated into individual catheters or other tubular devices, e.g., as described elsewhere herein and/or as disclosed in U.S. Publication No. 2009/0126862, the entire disclosure of which is expressly incorporated by reference herein.

With particular reference to FIG. 4A, the apparatus 50 may include one or more sources 52 of mandrels 2 and, optionally, one or more sources 54 of liner material 4, which may be fed into a guide 60 to define lumens of the tubular bodies 8. For example, a first reel 52a may include an elongate primary mandrel 2a, e.g., shaped and/or configured to define a primary or central lumen (not shown) of the tubular bodies 8. Similarly, a second reel 52b may include an elongate auxiliary mandrel 2b, e.g., shaped and/or configured to define a secondary or auxiliary lumen (also not shown) of the tubular bodies 8. Optionally, if additional lumens are desired for the tubular bodies 8, one or more additional auxiliary mandrels may be provided (not shown).

The mandrels 2 may have desired cross-sectional shapes and/or sizes corresponding to the desired cross-sections of the lumens, e.g., substantially circular or other shapes, as described elsewhere herein. The mandrels 2 may be a solid or hollow wire or other cylindrical member having a diameter (or other cross-section) corresponding to the diameter of the lumen to be lined by the strip, e.g., between about 0.005-0.300 inch (0.125-7.5 mm), 0.014-0.092 inch (0.35-2.3 mm), or 0.014-0.045 inch (0.35-1.15 mm). In an exemplary embodiment, the auxiliary mandrel 2b may have a substantially smaller diameter or other cross-section than the primary mandrel 2a. In exemplary embodiments, the mandrels 2 may be formed from beading or monofilament material, for example, lubricious material, e.g., PTFE or other fluoropolymer, silicone-treated Acetal, PTFE-coated stainless steel, Parylene-coated stainless steel, and the like, having sufficient flexibility to allow the mandrels 2 to be wound onto a source reel 52 and/or onto a take-up reel (not shown) after being incorporated into a tubular body 8.

Alternatively or in addition, the mandrels 2 may have a tubular liner predisposed about them, e.g. a fluoropolymer sleeve or coating or other tubular material which may facilitate removal of the mandrel 2 and/or be left behind upon removal of the mandrel 2 to form a liner. Further alternatively, a shim (not shown) may be positioned over a mandrel 2 and/or within a tubular or strip liner such that the shim (not shown) may facilitate creation of a lumen that is larger than the mandrel 2 with or without ultimate removal of the mandrel 2. For example, a PTFE tube or strip shim (not shown) may be positioned around a mandrel 2 and inside of a strip or tubular liner. The mandrel/shim/liner assembly may then be incorporated into a braided shaft or finished apparatus. The shim (not shown) may be subsequently removed, e.g. after braiding, lamination, etc. to leave a lumen larger than the mandrel. After this, the mandrel may remain in place, for example in the case of the auxiliary mandrel 2b to serve as a pull wire, or simply removed with less force.

In an alternative embodiment, the mandrels 2 may be formed from material that substantially maintains its size and shape during fabrication of the tubular bodies, yet may be reduced in cross-section after fabrication to facilitate removal. For example, silver-coated copper wire or other malleable metals may be used for the mandrels 2 that, after fabrication of the tubular body 8, may be necked down before being removed. For example, after fabricating a tubular body 8, the mandrels 2 (or the entire tubular body) may be pulled at each end, thereby causing the mandrels 2 to plastically elongate and thereby reduce their outer cross-section slightly, which may reduce friction between the mandrels 2 and the surrounding liners, reinforcement members, and/or other materials, and thereby facilitate removal. Further alternatively, the mandrels 2 may include a rolled strip with inherent radial strength capable of supporting a lumen during braiding and/or lamination and/or other processing, but may subsequently be constrained, stretched, or otherwise removed. Further alternatively, the mandrels 2 may be constructed from material having relatively high thermal expansion such that during heating, lamination, and/or reflow, the mandrels 2 expand and upon cooling contract, thereby creating a lumen larger than the original mandrel 2.

In yet another alternative, the mandrels 2 may be formed from materials that may be dissolved, e.g., after fabrication, leaving the surrounding materials intact to define the lumens.

In still another alternative, tubular mandrels may be used that have sufficient hoop strength to resist deformation under the forces encountered during braiding and/or other fabrication and/or heating or other processing parameters experienced during fabrication. In this alternative, the tubular mandrels may remain substantially within the tubular bodies 8 after fabrication, e.g., to define the auxiliary lumen. For example, a relatively thick walled PTFE, a lined or bare polymide tube, or other tubular mandrel may be used. Alternatively, the inner diameter of such a tubular mandrel may be temporarily supported by a temporary supporting mandrel (not shown), e.g. during braiding, and the temporary supporting mandrel may be removed prior to subsequent fabrication and/or heating or other processing steps, e.g., if the tubular mandrel is to remain as a permanent component of the tubular bodies.

Optionally, a source 54 of liner material 4 may be provided for the one or both mandrels 2. For example, as shown, a source 54a of liner material 4a is provided such that the liner material 4a may be wrapped at least partially around the primary mandrel 2a, e.g., as the primary mandrel 2a and liner material 4a are fed through the guide 60. The liner material 4a may be formed from lubricious material and/or may include one or more coatings (not shown) on an inner surface thereof oriented towards the primary mandrel 2a, which may provide an inner liner for a primary lumen of the resulting tubular bodies 8a.

For example, the liner material may include a base material, e.g., a relatively thin-walled polymer sheet having a width corresponding to the circumference of the corresponding mandrel, e.g., thermoplastics, such as polyether block amide, urethane, nylon, and the like, fluoropolymers, such as PTFE, FEP, TFE, and the like, thermoset, and thermoform plastics, such as polyimide or polyester, and the like. In exemplary embodiments, the liner material may have a thickness between about 0.0001-0.050 inch (0.0025-1.25 mm), 0.0001-0.003 inch (0.0025-0.076 mm), 0.0001-0.0015 inch (0.0025-0.038 mm), or 0.0005-0.002 inch (0.0125-0.05 mm).

Optionally, if desired a source of liner material may also be provided for the auxiliary mandrel 2*b* and/or for other auxiliary mandrels (not shown for simplicity). In this option, a guide (not shown) may be provided for wrapping the liner material around the auxiliary mandrel 2*b*, e.g., before the auxiliary mandrel 2*b* is positioned adjacent the primary mandrel 2*a*. In an alternative embodiment, tubular liner material may be provided on one or both mandrels when loaded on the source 52, and/or may be fed onto the desired mandrel in discrete segments (not shown) before passing the mandrels 2 through the guide 60 or horn gear 72.

With additional reference to FIGS. 4A and 4B, the source 70 of reinforcement members 6 may provide one or more, e.g., a plurality of, reinforcement members 6 that may be wrapped around the mandrels 2, e.g., upon exiting the guide 60. In the exemplary embodiment shown in FIG. 4B, the reinforcement source 70 may include an arrangement of horn gears 72, e.g., mounted in a generally circular configuration around the guide 60, for example, to a base or other support structure 76. The horn gears 72 may be free to rotate about their individual central axes but may be substantially fixed translationally relative to one another and the guide 60. Alternatively, the horn gears 72 may be rotatable relative to the guide 60, e.g., around a central axis of the guide 60, while maintaining their same circular configuration, e.g., by rotating the base 76 relative to the guide 60, as described further elsewhere herein.

In addition, one of the horn gears 72*a* may include a passage 73*a* therethrough, e.g., aligned with the central axis of the horn gear 72*a*, and the auxiliary mandrel 2*b* may pass through the passage 73*a*, e.g., from the source 52*b* towards the primary mandrel 2*a* where it exits the guide 60. If liner material is wrapped or otherwise disposed around the auxiliary mandrel 2*b*, a guide (not shown) may be provided before, after, or within the passage 73*a* to wrap or otherwise dispose the liner material around the auxiliary mandrel 2*b*. Optionally, if additional auxiliary lumens are to be provided in the tubular bodies 8, one or more additional horn gears may also include such passage(s) and/or guide(s) for guiding corresponding auxiliary mandrel(s) therethrough. It will be appreciated that the number of auxiliary lumens available for the tubular bodies may be limited by the number of horn gears 72 in the reinforcement source 70 (unless multiple mandrels and/or liners are directed through a single passage, e.g., to form a lumen, such as that shown in FIG. 6F. For example, in the embodiment shown in FIG. 4B, six horn gears 72 are provided and so six auxiliary mandrels may be provided that pass through respective horn gears 72. The number of horn gears may be increased or decreased, as desired, to provide a desired number of reinforcement members and/or auxiliary lumens, e.g., four, eight, twelve, sixteen, or other numbers of horn gears (not shown), or other generally symmetrical configuration.

Optionally, if desired, individual carriers may be loaded with multiple reinforcement members (not shown), e.g., such that multiple reinforcement members are braided adjacent one another in each direction from each carrier.

Figure 8:
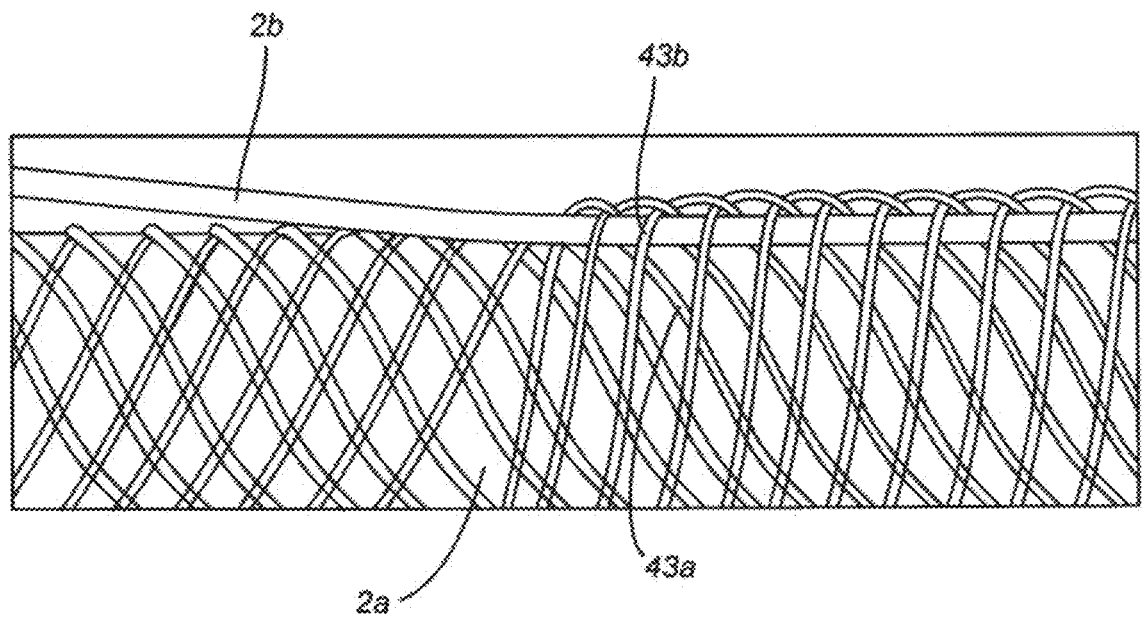
FIG. 8 is a detail of a reinforcement-wrapped mandrel assembly including an auxiliary mandrel including a portion that exits from reinforcement members surrounding a primary mandrel.

In the exemplary embodiment shown in FIG. 8, a first set of reinforcement members 43*a* may travel and be braided in a first direction by the horn gears 72 such that all of the windings of the first set 43*a* pass between the auxiliary mandrel 2*b* and the primary mandrel 2*a* at that specific horn gear. A second set of reinforcement members 43*b* may travel and be braided in a second opposite direction by the horn gears 72 such that all of the windings of the second set 43*b* pass over the auxiliary mandrel 2*b* at that specific horn gear. Otherwise, the reinforcement members may pass over and under one another according to the arrangement of horn gears 72 and carriers 74 loaded onto the reinforcement source 70, which pattern generally alternates at each subsequent horn gear.

In addition, one of the horn gears 72*a* may include a passage 73*a* therethrough, e.g., aligned with the central axis of the horn gear 72*a*, and the auxiliary mandrel 2*b* may pass through the passage 73*a*, e.g., from the source 52*b* towards the primary mandrel 2*a* where it exits the guide 60. If liner material is wrapped or otherwise disposed around the auxiliary mandrel 2*b*, a guide (not shown) may be provided before, after, or within the passage 73*a* to wrap or otherwise dispose the liner material around the auxiliary mandrel 2*b*. Optionally, if additional auxiliary lumens are to be provided in the tubular bodies 8, one or more additional horn gears may also include such passage(s) and/or guide(s) for guiding corresponding auxiliary mandrel(s) therethrough. It will be appreciated that the number of auxiliary lumens available for the tubular bodies may be limited by the number of horn gears 72 in the reinforcement source 70 (unless multiple mandrels and/or liners are directed through a single passage, e.g., to form a lumen, such as that shown in FIG. 6F. For example, in the embodiment shown in FIG. 4B, six horn gears 72 are provided and so six auxiliary mandrels may be provided that pass through respective horn gears 72. The number of horn gears may be increased or decreased, as desired, to provide a desired number of reinforcement members and/or auxiliary lumens, e.g., four, eight, twelve, sixteen, or other numbers of horn gears (not shown), or other generally symmetrical configuration.

Figure 4D:
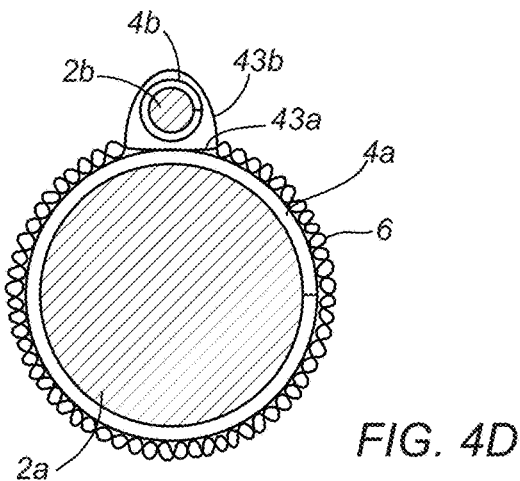
FIG. 4D is a cross-section of the braided mandrels of FIG. 4C, taken along line 4D-4D.

With further reference to FIG. 4C, as can be seen, the primary mandrel 2*a* may exit the guide 60 with the liner material 4*a* being wrapped substantially around the primary mandrel 2*a*. The auxiliary mandrel 2*b* may be directed towards the primary mandrel 2*a* such that the auxiliary mandrel 2*b* is disposed immediately adjacent the primary mandrel 2*a*, e.g., at the location where the reinforcement members 6 converge on the primary mandrel 2*a*. During operation, the reinforcement members 6 may be braided around the primary mandrel 2*a* such that some of the windings 43 pass over the auxiliary mandrel 2*b* and others pass under the auxiliary mandrel 2*b*, e.g., as shown in FIG. 4C. More particularly, given the configuration of horn gears in FIGS. 4A and 4B, half of the reinforcement members 6 are wrapped in a first, e.g., clockwise, direction, with alternate windings passing over and under the auxiliary mandrel 2*b*, and half of the reinforcement members 6 are wrapped in a second, e.g., counterclockwise, direction with alternate windings passage over and under the auxiliary mandrel 2*b*. Thus, in this manner, all of the reinforcement members 6 may surround the primary mandrel 2*a*, while only some windings 43*a* may surround the auxiliary mandrel 2*b*, as shown in FIG. 4D. In an exemplary configuration, all of the carriers 74 passing in the first direction may cause their reinforcement members to pass over the reinforcement members of the carriers 74 passing in the second direction.

The drive mechanism 80 may include one or more components for pulling or otherwise directing the mandrels 2 through the apparatus 50. For example, the drive mechanism 80 may include a pair of spaced-apart rollers 82 coupled to a motor (not shown) that engage the reinforcement-wrapped mandrels 2 and apply sufficient tension to pull the mandrels 2 from their sources 52 through the guide 60 and/or horn gear 72*a* while the reinforcement members 6 are braided around the mandrels 2. Alternatively, the drive mechanism may be provided before the reinforcement members 6 are braided around the mandrels 2, e.g., pushing the primary mandrel 2*a* through the braiding operation and potentially pulling the auxiliary mandrel 2*b* by the braiding action itself. Optionally, other drive mechanisms and/or tension adjusters (not shown) may be provided for maintaining a desired tension and/or otherwise guiding the mandrels 2, liners 4, reinforcement members 6, and assembled device in a desired manner along the fabrication path.

Optionally, as shown in FIG. 4A, the jacket source 90 may be provided for applying one or more layers of jacket material around the reinforcement-wrapped mandrels 2. For example, a co-extruder, laminator, or other applicator may be provided that applies melted, uncured, and/or otherwise raw jacket material 7, e.g., from a hopper or other container (not shown), or rolls sheets of jacket material 7 may be wrapped around the reinforcement members 43 and mandrels 2.

For example, for thermoplastic or other flowable materials, a heater (not shown) within a co-extruder may melt or otherwise soften the jacket material 7 to allow the jacket material 7 to flow around the reinforcement members 43 and into contact with the liner material 4 surrounding the mandrels 2 (or the mandrels 2 directly if no liner material is provided). Alternatively, the jacket material 7 may be a thermoset plastic or other material such that components of the jacket material 7 may be delivered into the co-extruder, e.g., as a liquid, powder, and the like, and mixed to form a slurry that is delivered around the reinforcement-wrapped mandrels 2. The components may chemically or otherwise react with one another and/or be heat fused to form a solid jacket 7 once cured. Exemplary materials for the jacket material 7 include plastics, e.g., thermoplastics, such as polyether block amide, nylon, or urethanes, thermoset plastics, metals, or composite materials. Alternatively, other processing may be used to bond or otherwise attach the jacket material 7 to the liner material 4 and/or embed the reinforcement members 43 in the jacket material 7, thereby resulting in an integral tubular body 8.

The resulting tubular body 8 (with or without jacket material 7) may be collected, e.g., on a capture reel or in a container (not shown). Thereafter, the tubular body 8 may be further processed to make a catheter, sheath, or other device. For example, a cutter or other tool (not shown) may separate the tubular body 8 into individual tubular shafts, e.g., before or after removing the mandrels 2. For example, the mandrels 2 may remain within the tubular body 8 when cut into individual devices, and then may be removed, resulting in a primary lumen and an auxiliary lumen, e.g., similar to the apparatus 10 shown in FIG. 1B. Alternatively, if the friction between the mandrels 2 and the surrounding material is relatively low, the mandrels 2 may be removed before the tubular body 8 is cut into individual devices.

The resulting inner surface 41*a* of the primary lumen 18*a* may have a substantially uniform cross-section, e.g., as shown in FIG. 1B. Similar the auxiliary lumen 18*b* may also have a substantially uniform cross-section, e.g., as shown in FIG. 1C. Alternatively, the inner surface 41*b* of the auxiliary lumen 18*b* may have a variable cross-section. Such a variable cross-section may be achieved by controlling one or more parameters during fabrication. For example, such variables may include a) the tension applied when the reinforcement members 6 are wrapped around the auxiliary mandrel 2*b*, b) the softness and/or elasticity of the auxiliary mandrel 2*b*, c) the tension applied to the auxiliary mandrel 2*b* as it is directed into contact with the primary mandrel 2*a*, and/or d) the material of liner material around the auxiliary mandrel 2*b*.

In an exemplary embodiment, the reinforcement materials 43*a* may be formed from material having a lower coefficient of friction than the surrounding jacketing material (e.g., if no liner material is applied), which may decrease the frictional resistance of the steering element (not shown) within the auxiliary lumen 18*b* when it slides along the reinforcement members 43*a*. In addition or alternatively, as shown in FIG. 1B, the increased cross-section between the reinforcement members 43*a* may minimize or entirely avoid contact between the steering element and the material surrounding the auxiliary lumen 18*b* between the reinforcement members 43*a*.

Other components may be added to the individual tubular devices, as desired for the particular application. For example, for a steerable catheter, a steering element may be inserted through the auxiliary lumen created when the auxiliary mandrel 2*b* is removed. In an alternative embodiment, the auxiliary mandrel 2*b* may remain within the tubular device to provide the steering element, e.g., if the friction between the outer surface of the auxiliary mandrel 2*b* and the liner or other material defining the auxiliary lumen are relatively low. A tip or other component may be attached to a distal end of the tubular device, e.g., after attaching one end of the steering element to the tip. The other end of the steering element may be coupled to an actuator of a handle attached to a proximal end of the tubular device, e.g., similar to embodiments described elsewhere herein.

In another method, the apparatus 50 may be used to create an auxiliary lumen (or multiple auxiliary lumens, if desired) that extend helically around at least a portion of the primary lumen. For example, as described above, the base 76 and horn gears 72 of the reinforcement source 70 may remain substantially fixed relative to the guide 60 and drive mechanism 80, which results in the auxiliary mandrel 2*b* extending substantially parallel and adjacent to the primary mandrel 2*a*. Consequently, this method results in an auxiliary lumen that also extends substantially parallel and adjacent to a primary or central lumen, e.g., as shown in FIG. 1B.

Alternatively, the base 76 may be rotatable relative to the guide 60 and drive mechanism 80, e.g., coupled to a motor or other driver that may selectively or continuously rotate the base 76, thereby rotating the horn gears 72 around the guide 60. Consequently, in this alternative, the horn gear 72*a* including the passage 73*a* for the auxiliary mandrel 2*b* may rotate relative to the primary mandrel 2*a*, thereby directing the auxiliary mandrel 2*b* spirally around the primary mandrel 2*a* as the reinforcement members 6 are braided around them.

This rotation may be driven at a desired, e.g., fixed or variable, speed to result in a desired, e.g., fixed or variable, distance between adjacent windings of the auxiliary mandrel 2*b* around the primary mandrel 2*a*. The rotation may be maintained substantially continuously, e.g., if it is desired for the auxiliary mandrel 2*b* to spiral along the entire length of the primary mandrel 2*a*, or for desired limited time periods, e.g., resulting in sections of the tubular body 8 where the auxiliary mandrel 2*b* spirals around the primary mandrel 2*a* for desired lengths separated by sections where the auxiliary mandrel 2*b* extends substantially parallel to the primary mandrel 2*a*.

In an alternative embodiment, the base 76 and horn gears 72 may be fixed, and instead the drive mechanism 70 may be rotated, e.g., to rotate the reinforcement-wrapped mandrels 2 relative to the earlier components of the apparatus 50. For example, the rollers 72 may be rotated about the central axis while engaging the reinforcement-wrapped mandrels 2 to cause the entire assembly to rotate, causing the auxiliary mandrel 2b to spiral relative to the primary mandrel 2a before or as the reinforcement members 6 are braided on.

In an exemplary embodiment, the apparatus 50 may be alternated between fixed and rotating operations, thereby alternatively spiraling the auxiliary mandrel 2b around the primary mandrel 2a and directing the auxiliary mandrel 2b substantially parallel to the primary mandrel 2a. The resulting tubular body 8 may be separated into multiple devices having spiral and straight sections of the auxiliary mandrel 2b, which may then be incorporated into individual catheters or other devices. Consequently, this method may result in an auxiliary lumen that spirals around a primary or central lumen along a portion of a tubular device (e.g., an intermediate and/or proximal portion), and extends substantially parallel and adjacent to the central lumen along another portion (e.g., a distal portion), e.g., similar to the apparatus 110 shown in FIG. 2.

One of the advantages of the methods for making tubular bodies described herein is that the reinforcement members, in addition to providing desired reinforcement in the final devices, may also substantially secure the mandrels 2 and/or other components of the tubular bodies during fabrication. For example, one potential problem with using multiple tubular members to fabricate a single device with multiple lumens is undesired movement between the components. With the methods described herein, the reinforcement members may substantially secure the mandrels 2 (and any liners surrounding them) relative to one another immediately upon braiding. For example, the reinforcement members may frictionally engage the mandrels or liners, or even partially embed into the liners, which may minimize the risk of these components subsequently moving relative to one another, particularly if jacketing is applied after collecting and/or storing the reinforcement-wrapped mandrels for a period of time.

In addition, the apparatus and methods herein may facilitate transitioning the auxiliary lumen at one or both ends of a tubular device. For example, as shown in FIG. 3, the apparatus 10 includes a transition within the handle 21 of the auxiliary lumen 18b out of the wall of the tubular member, e.g., to allow the steering element 30 to extend from the proximal end 12 such that the proximal end 32 may be coupled to the actuator 25.

To accomplish this, a portion of the auxiliary mandrel 2b may be disengaged from the braider such that the portion remains entirely outside the reinforcement members. FIG. 8 shows a detail of such a configuration. For example, after a desired portion of the auxiliary mandrel 2b has been braided to the primary mandrel 2a by the reinforcement members 6, the auxiliary mandrel 2b may be cut or otherwise separated from the horn gear 72 and positioned outside the braiding point. Thus, as reinforcement members 6 continue to be braided around the primary mandrel 2a, the auxiliary mandrel 2b remains outside the braid, as shown in FIG. 8.

Subsequently, when jacket material 7 is applied around the reinforcement-wrapped mandrels 2, the auxiliary mandrel 2b may extend out of the jacket material 7 at one end. When the auxiliary mandrel 2b is removed, a side port may be provided on the end of the jacketed tubular body that communicates with the resulting auxiliary lumen 18b. This end may be positioned inside the handle 21, e.g., as shown in FIG. 3, before or after inserting a steering element 30 through the auxiliary lumen 18b. With the proximal end 32 of the steering element 30 extending from the side port, the proximal end 32 may be coupled to the actuator 25, e.g., using conventional methods.

This method may provide a substantially uniform and consistent way to insert and couple steering element to a tubular device. In other extrusions or multiple lumen catheters (not shown), the side wall of the proximal may have to be slit or otherwise penetrated to access a steering element lumen therein and insert a steering element. Such skiving, slitting, or penetration may create a weak point in the wall of the tubular device and/or may risk puncturing into the primary lumen, e.g., such that air or other contaminants may communicate between the lumens of the tubular device. Such risks may be avoided by positioning the auxiliary mandrel 2b outside the reinforcement members at a region corresponding to the proximal end of the desired tubular device.

Figure 9:
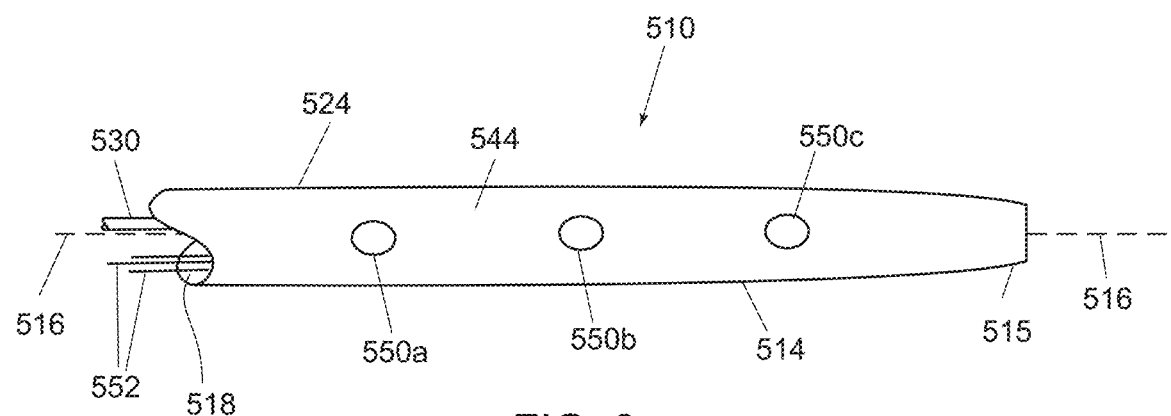
FIG. 9 is a side view of a distal portion of another exemplary embodiment of a catheter including a plurality of electrodes spaced apart from one another on the distal portion.

Turning to FIG. 9, another exemplary embodiment of a catheter or other apparatus 510 is shown that includes an elongate tubular member including a proximal end (not shown), a distal end 514, and a steerable distal portion 524 sized for insertion into a body lumen, a central longitudinal axis 516 extending between the proximal and distal ends 514, and one or more lumens 518 extending between the proximal and distal ends 514, constructed generally similar to other embodiments herein. For example, the catheter 510 may include a central or primary lumen extending from the proximal end to an outlet (not shown) in the distal end 514, e.g., to allow a guidewire, catheter, or other instrument (not shown) to pass therethrough and/or for delivering or aspirating fluid therethrough.

In addition, the catheter 510 may include one or more auxiliary lumens, e.g., extending adjacent the central lumen at least partially between the proximal and distal ends 514, e.g., substantially parallel to and radially offset relative to the central axis 516 at least along the distal portion 524. In an exemplary embodiment, the auxiliary lumen(s) may be a steering element lumen configured to slidably receive a pull wire or receive another steering element 530 therein, e.g., to bend or otherwise deflect the distal portion 524 of the apparatus 510, similar to other embodiments herein. Optionally, the catheter 510 may include one or more additional lumens (not shown), e.g., one or more additional steering element lumens, inflation lumens, and/or accessory lumens.

Generally, the apparatus 510 includes an inner liner 540, e.g., at least partially or entirely surrounding or otherwise defining the central lumen (shown in FIG. 10), a reinforcement layer 542 surrounding the inner liner 540 (also shown in FIG. 10), and an outer jacket 544 surrounding the reinforcement layer (shown in FIG. 9), each of which may extend at least partially between the proximal and distal ends 514 of the apparatus 510, as described elsewhere herein.

The distal portion 524 may include a tapered, rounded, or otherwise shaped distal tip 515, e.g., to provide a substantially atraumatic tip and/or to facilitate advancement or navigation through various anatomy. Optionally, the distal end 514 may include one or more features to enhance radiopacity and/or visibility under ultrasound, MRI or other imaging modalities (not shown), similar to other embodiments herein.

Optionally, similar to the apparatus 10 shown in FIG. 1A, the proximal end may include a handle or hub, which may include one or more ports, e.g., a port communicating with the central lumen, one or more actuators, e.g., for actuating the pull wire 530, and/or one or more connectors, e.g., for coupling a sensor and/or controller to the apparatus 10, also similar to other embodiments herein.

As shown in FIGS. 9 and 11A-11D, the catheter 510 includes a plurality of electrodes and/or sensing elements 550 on the distal portion 514 and a plurality of wires 552 extending proximally from the electrodes 550, e.g., to the proximal end and/or one or more connectors on or extending from the handle (not shown). As shown in FIG. 9, the electrodes 550 may be spaced apart from one another at predetermined intervals along the distal portion 524. Alternatively, or in addition to, one or more electrodes may be positioned more proximally on the catheter 510 (not shown). In the embodiment shown, the electrodes 550 are spot electrodes applied on one side of the distal portion 524 such that the electrodes 550 are aligned substantially axially relative to one another. Alternatively, one or more of the electrodes may be offset circumferentially from others (not shown), if desired. In a further alternative, the electrodes may comprise other non-circumferential or circumferential and/or other symmetric or asymmetric geometries, e.g., the electrodes may be a button, a patch, a square, a rectangle, a partial ring, a ring, a coil, or other type of electrodes that extend partially or completely around the circumference of the distal portion 524.

The electrodes 550 may be at least partially set into the wall of the distal portion 524, e.g., to provide a secure attachment and/or substantially smooth and/or atraumatic outer surface for the distal portion 524. For example, at least a portion of the outer layer 544 of the distal portion 514 may be removed, e.g., to provide a recess for the electrodes 550 and/or to expose the wires 552 or otherwise allow the wires 552 to be coupled to the electrodes 550, as described further elsewhere herein.

The wires 552 may be embedded within the wall of the distal portion 524, e.g., braided/positioned/embedded within elements of the reinforcement layer 542 adjacent a primary lumen and/or auxiliary lumen. In the embodiment shown in FIG. 10, a pair of wires 552' are shown immediately adjacent one another and adjacent a mandrel/liner 502 for forming an auxiliary lumen and oriented such that the wires 552 extend substantially parallel to the longitudinal axis 516 of the apparatus 510. One disadvantage of orienting the wires 552 substantially axially along the distal portion 524 is that the wires may be subjected to tension and/or compression during use of the apparatus 510, which may risk damaging the wires 552 during use of the apparatus 510.

For example, when the distal portion 524 is deflected into a curved configuration, if the wires 552 are on the outside of the bend, the wires 552 may be subjected to axial tension, and conversely, if the wires 552 are on the inside of the bend, the wires 552 may be subjected to axial compression, risking buckling or kinking. In particular, wires 552 may be formed from relatively inelastic and/or ductile material, e.g., copper, and the like, which may not accommodate repeated bending and risk of cracking or breaking, which may create a hot spot, short, and/or interference/artifact in sensed signals.

In addition, orienting the wires 552 substantially axially may modify the intended bending forces applied by the steering element 530 of the apparatus 510 in an undesirable manner. However, the wires 552 may be positioned at a desired circumferential location, e.g., to minimize interaction of the wires 552 with the deflection of the distal portion 524 during use. For example, the wires 552 may be positioned substantially along a side of the distal portion 524 corresponding to a neutral axis of the distal portion 524, e.g., offset about ninety degrees (90°) from the deflection plane of the distal portion 524.

In an alternative embodiment, the wires 552 may be oriented within the distal portion 524 in a configuration to accommodate bending or deflection of the distal portion 524. For example, as shown in FIGS. 11A-11D, three wires 552 are shown that extend along the distal portion 524 in a generally sinusoidal pattern immediately adjacent one another, optionally substantially centered on the neutral axis of the distal portion 524. Such a curvilinear arrangement may accommodate bending by distributing the forces acting on the wires 552 and/or allow the wires 552 to accommodate changes in path length of the catheter 510 during use or manipulation. In addition or alternatively, patterns/configurations other than the sinusoidal pattern shown may be used to introduce excess path length of the wires 552 as they are incorporated into the reinforcement layer 542.

In another alternative, the wires 552 may be embedded within the reinforcement layer 542 such that the wires 552 extend helically around the primary lumen, e.g., similar to the auxiliary lumen shown in FIG. 2. In this manner, the wires 552 may be distributed relatively uniformly around the central axis 516, thereby minimizing impact of path length changes when bending forces applied by the steering element 530.

In still another alternative, a wire lumen may be provided within the distal portion 524, e.g., embedded within the reinforcement layer 542 similar to the auxiliary lumens described elsewhere herein, and the wires 552 may be slidably disposed within the wire lumen.

Figure 11A:
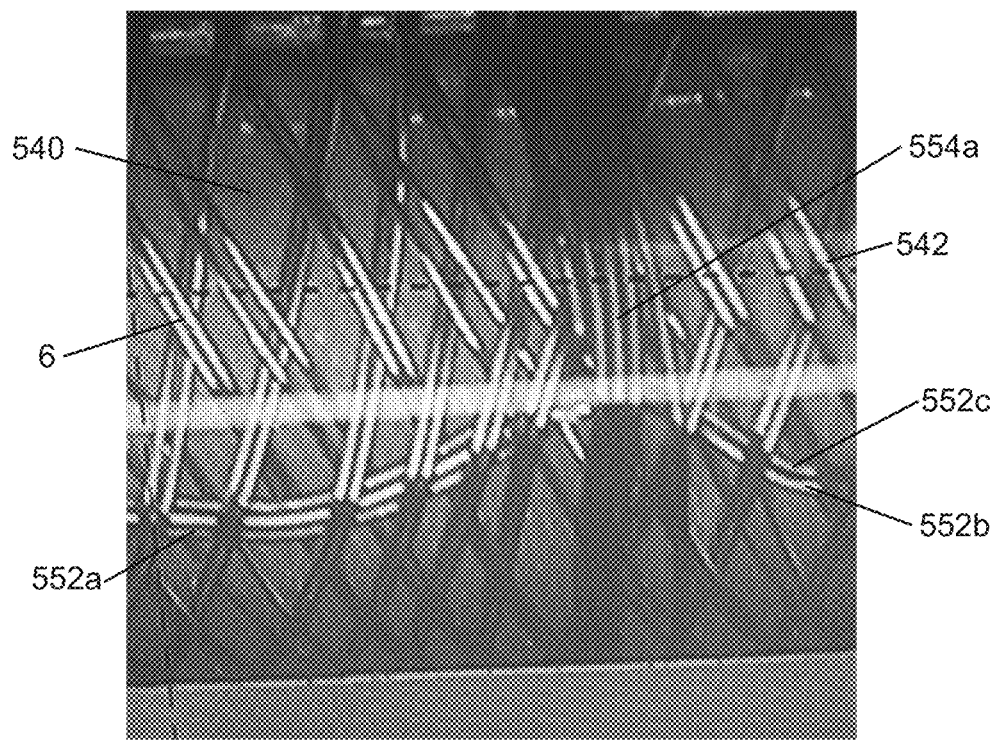
FIGS. 11A-11D are details showing a method for braiding a plurality of wires of a catheter within a plurality reinforcement members and coupling electrodes to the wires.
Figure 11B:
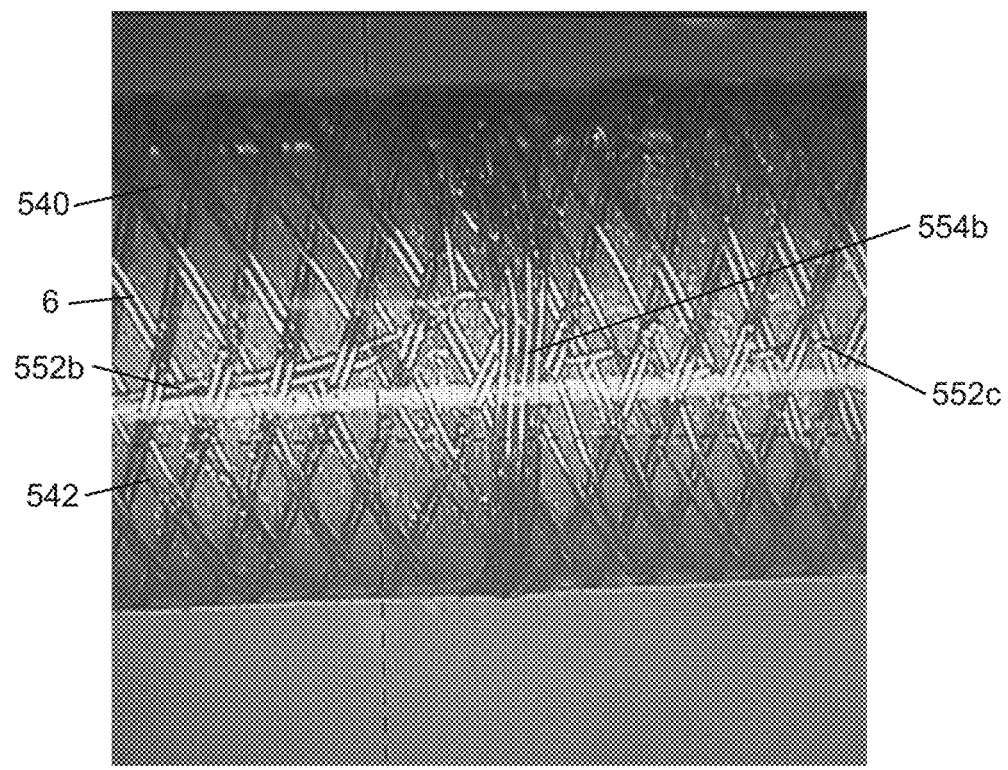
Figure 11C:
Figure 11D:
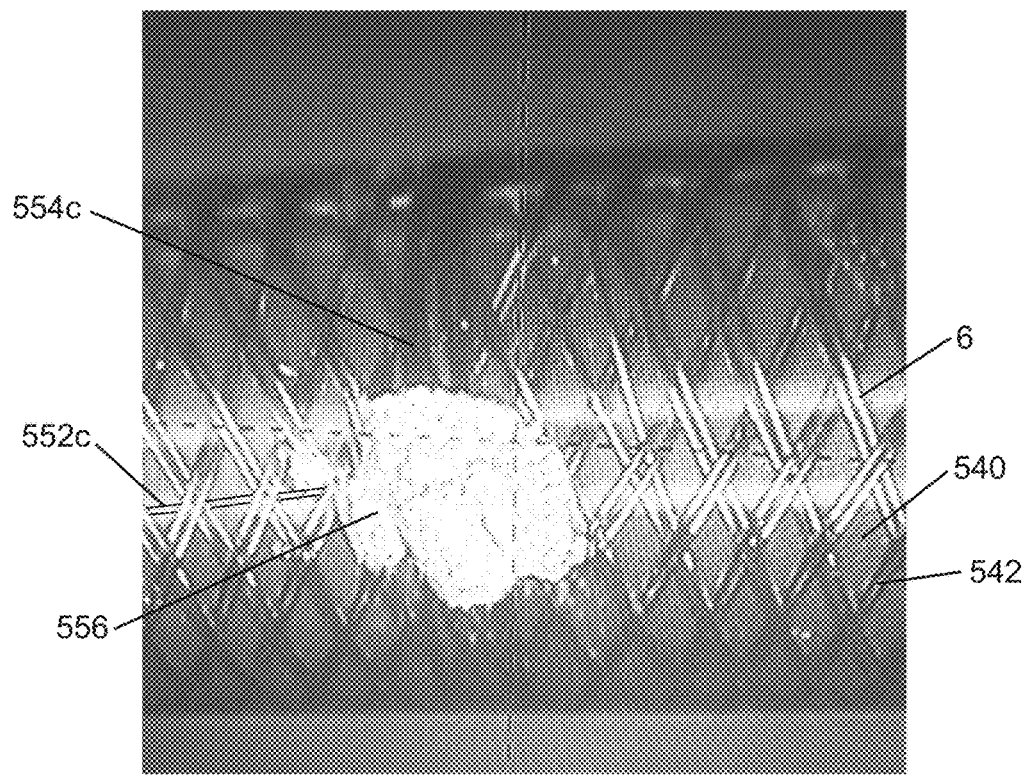
Figure 11E:
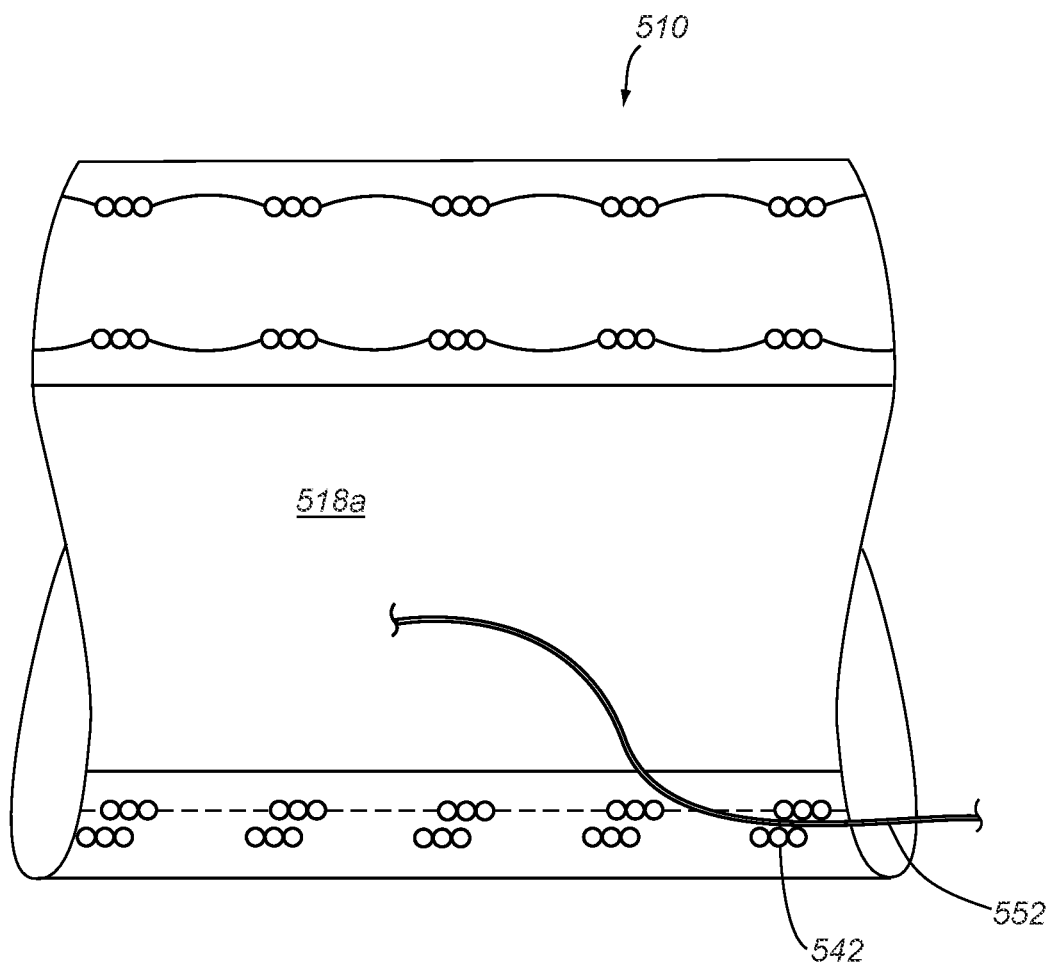
FIG. 11E is a cross-sectional view of an intermediate portion of an apparatus showing a wire transitioning to a central lumen of the apparatus.

Optionally, e.g., as shown in FIG. 11E, in an intermediate or proximal portion of the apparatus 510, the wires 552 may transition to a large central lumen 518a containing other components of the apparatus 510, e.g., similar to other embodiments herein.

Although the plurality of wires 552 may be arranged such that they are disposed immediately adjacent or against one another (or disposed within the wire lumen), alternatively, the wires 552 may be provided at different circumferential locations relative to one another (not shown), yet still be embedded within the reinforcement layer 542. For example, the wires 552 may be spaced apart substantially evenly around the primary lumen (e.g., offset about one hundred eighty degrees for a pair or wires, about one hundred twenty degrees for three wires, and the like) and may be oriented in a desired configuration, e.g., substantially axially, in a curvilinear path, or helically, while remaining spaced apart from one another.

With additional reference to FIGS. 11A-11D, various methods may be used for manufacturing and/or assembling the apparatus 510 or any of the other variations described herein. For example, one or more tubular bodies including embedded wires may be produced using a substantially continuous process, e.g., similar to the apparatus and methods described elsewhere herein with reference to FIGS. 4A-4C. For example, the methods may be used to make a relatively short tubular body corresponding to a single catheter, or may be used to make a relatively long tubular body that may be subsequently separated into individual catheter bodies. The composition of the components for the apparatus 510 and construction and operation of an apparatus for making the apparatus 510 may be similar to those described with reference to FIGS. 4A-4C elsewhere herein, and so components of the apparatus 50 are referenced below where applicable.

Generally, similar to the apparatus 50 shown in FIG. 4A, an exemplary manufacturing apparatus for making the apparatus 510 may include one or more sources 52, 54 of mandrels 2 and/or liners 4 (e.g., to form the primary lumen and one or more auxiliary lumens), a source of wires (e.g., one or more reels carrying individual or a plurality of wires, not shown), a guide 60, a source 70 of reinforcement members 6, a drive mechanism 80, and, optionally, a source 90 of jacket material 7. The apparatus 50 may allow for substantially continuous fabrication of tubular bodies, e.g., wrapping a liner material 4a around a primary mandrel 2a, positioning an auxiliary mandrel 2b (with optional liner material) adjacent the primary mandrel 2a, positioning the set of wires adjacent the primary mandrel 2a, and braiding a plurality of reinforcement members 4 around the mandrels 2 and wires. In an alternative embodiment, where the wires are provided within a lumen, an additional mandrel source (with optional liner, both not shown) may be provided instead of the source of wires, and the additional mandrel may be positioned adjacent the primary mandrel 2a, e.g., at a desired circumferential location, such as aligned with the intended neutral axis of the final tubular device. For example, the lumen (or wires) may be offset from the auxiliary mandrel 2b about ninety degrees (90°) circumferentially around the primary mandrel 2a.

During operation, liner material 4a may be wrapped at least partially around the primary mandrel 2a, e.g., as the primary mandrel 2a and liner material 4a are fed through the guide 60. The auxiliary mandrel 2a and wires may be positioned adjacent the liner-wrapped primary mandrel 2a, and reinforcement members 6 may be wrapped around the mandrels 2 and wires, e.g., upon exiting the guide 60 to braid the auxiliary mandrel 2b and wires within the reinforcement members 6.

In the exemplary embodiment shown in FIG. 4B, the reinforcement source 70 may include an arrangement of horn gears 72, e.g., mounted in a generally circular configuration around the guide 60, for example, to a base or other support structure 76. One of the horn gears 72a may include a passage 73a therethrough, and the auxiliary mandrel 2b may pass through the passage 73a, e.g., from the source 52b towards the primary mandrel 2a where it exits the guide 60. Similarly, a set of wires may be directed through a central passage in another of the horn gears (not shown) towards the primary mandrel 2a where it exits the guide 60 (or individual wires may be directed through separate central passages towards the primary mandrel 2a). Optionally, if additional auxiliary lumens or separate wires are to be provided in the tubular bodies 8, one or more additional horn gears may also include such passage(s) for guiding corresponding auxiliary mandrel(s) and/or wire(s) therethrough.

As a result of this process, some reinforcement members 6 pass between the primary mandrel 2a and the wires, some reinforcement members 6 pass between the primary mandrel 2a and the auxiliary mandrel 2b, and some reinforcement members 6 surround both the primary mandrel 2a and one or both of the auxiliary mandrel 2b and the wires. Thus, as can be seen in FIGS. 11A-11D, the wires 552 may be braided/incorporated into the reinforcement members 6 of the reinforcement layer 542, similar to the auxiliary mandrel 2b as described in other embodiments herein. Such a configuration may minimize the impact of the wires 552 on the outer profile of the resulting tubular body, ensure security of the wires 552, and/or increase ease of incorporation of the wires 552 into the tubular body. In addition, the reinforcement members 6 may constrain the wires 552, e.g., to minimize the wires interfering with subsequent processing of the tubular body. The reinforcement members 6 may include various metal alloys, plastic filaments, glass fibers and the like, as is known in the art. The profile of reinforcement members 6 may be substantially round, rectangular, and or have other cross-sectional profile as is also known in the art. The size of the reinforcement members 6 may range from about 0.0005" to 0.010" and more than one size may be used. In an exemplary embodiment, the reinforcement members 6 may be stainless steel round wire, e.g., to avoid damage to insulation on the wires 552. In an alternative embodiment (not shown), the reinforcement members 6 passing under the wires 552 may comprise a rectangular cross section while the reinforcement members 6 passing over the wires 552 may comprise a round cross-section, e.g. to reduce potential for damage to the wires 552 or their insulation.

Figure 10:
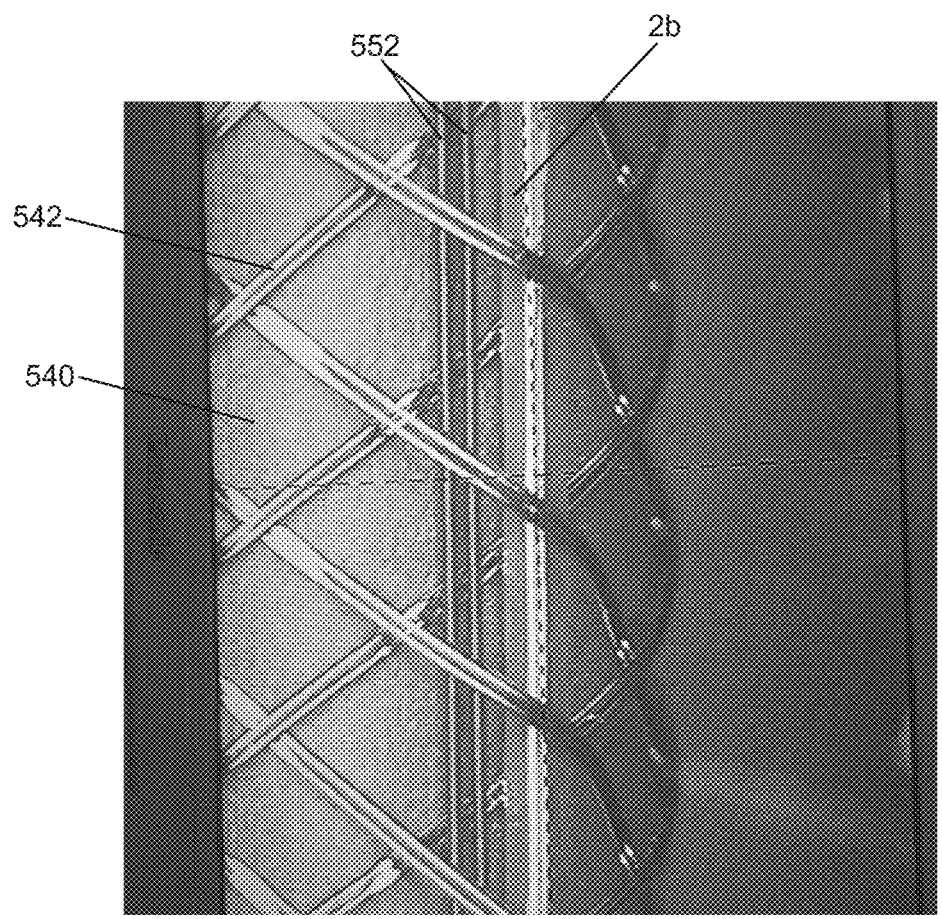
FIG. 10 is a detail of a reinforcement-wrapped mandrel assembly for making the catheter of FIG. 9, showing a plurality of wires extending along a portion of the catheter adjacent a pull wire lumen and braided into a plurality of reinforcement members.

The apparatus 50 may be operated such that the wires extend in a curvilinear path along the length of the primary mandrel, as shown in FIG. 11A. For example, a guide (not shown) may be provided adjacent the guide 60 that oscillates or otherwise moves to place the wires generally axially but in sinusoidal or other pattern of increased path length against the primary mandrel. Alternatively, the wires may be fed intermittently at a rate faster than the braiding feed rate, e.g. to incorporate excess path length of the wire into the braided assembly. Further alternatively, if desired, the wires may be wound helically around the primary mandrel, e.g., similar to the method described elsewhere herein with reference to FIG. 2, or may be directed substantially axially (e.g., as shown in FIG. 10).

In addition, the apparatus and methods herein may facilitate transitioning the wires at one or both ends of a tubular device. For example, as shown in FIG. 11A, three wires 552 are shown captured within the reinforcement members 6. The wires may extend together along the primary mandrel (e.g., from an intermediate region or the proximal end) until a first location where an electrode or sensing element is to be provided on the apparatus 510. A first wire (or set of wires), e.g., corresponding to wire 552a in FIG. 11A, may be disengaged from the braider such that the first wire remains entirely outside the reinforcement members 6.

For example, after a desired portion of the three wires 552 has been braided to the primary mandrel 2a by the reinforcement members 6, the first wire may be cut or otherwise separated from the horn gear and/or otherwise positioned outside the braiding point. Thus, as reinforcement members 6 continue to be braided around the primary mandrel 2a, the first wire 552a remains outside the braid, and only the second and third wires 552b, 552c are captured by the braid, as can be seen in FIG. 11B. Similarly, when a second electrode location is reached, the second wire may be disengaged from the braider such that the second wire remains entirely outside the reinforcement members 6. Further braiding captures only the third wire 552c, as shown in FIG. 11C. When a third electrode location is reached, the third wire may be disengaged from the braider such that the third wire remains entirely outside the reinforcement members 6. Any further desired braiding may then be performed on the primary and auxiliary mandrels 2. Thus, thereafter, all of the wires 552 remain outside the reinforcement members 6.

Thereafter, one or more layers of jacket material 7 may be applied around the reinforcement-wrapped mandrels 2. For example, with reference to FIGS. 4A-4C, a co-extruder, laminator, or other applicator may be provided that applies melted, uncured, and/or otherwise raw jacket material 7, e.g., from a hopper or other container (not shown), or rolls sheets of jacket material 7 may be wrapped around the reinforcement members 43 and mandrels 2.

Optionally, a length of each wire 552 may be maintained to at least partially form an electrode or sensing element. For example, as shown in FIGS. 11A-11C, the free end of each wire 552 may have sufficient length, e.g., between about one and ten centimeters (1-10 cm), such that the free end may be wound one or more times around the assembly, e.g., to define coils 554. The coils 554 may be created before applying the jacket material 7 such that the coils 554 are embedded in the jacket material (not shown in FIGS. 11A-11C). Alternatively, the coils 554 may be wrapped around the outer jacket 524, e.g., within annular grooves formed in the outer jacket 524 or simply around the outer surface (not shown). In this alternative, the coils 554 may be secured to the outer jacket 524, e.g., by interference fit, bonding with adhesive, and the like. Optionally, an insulating layer may be at least partially removed from the coils 554 to electrically expose the coils 554 for sensing and/or energy delivery. Alternatively, an insulating layer may be at least partially applied over the coils 554 to electrically isolate them and/or protect the coils 554 from corrosion or other undesired exposure.

Optionally, if the resulting tubular device corresponds to multiple catheter bodies, the tubular device may be separated into individual catheter bodies, each having a desired number of coils 554 and wires 552, e.g., three as shown in FIGS. 9 and 11A-11C. Alternatively, individual catheter bodies may be formed using the apparatus 50, similar to other embodiments herein.

After (or optionally before) separating the tubular device into individual catheters, electrodes may be built on the outer surfaces at the locations of wire exit and/or coils 544. Optionally, at least a portion of the insulation on the free end of each wire 552 may be removed, if desired, to facilitate electrically coupling the wire 552 to other components of the electrode 550. For example, if the jacket material has been applied, a portion of the jacket material overlying each coil 554 may be removed, and then the insulation on the outer surface of each coil 554 may be removed such that the coil 554 remains electrically isolated from the reinforcement members 6 but an electrically conductive contact surface is provided.

Then, as shown in FIG. 11D, a biocompatible electrically conductive polymer, adhesive, epoxy, solder, and/or other material 556 may bonded or otherwise conductively attached to the conductive wire 556 where the insulation and jacket material has been removed. As shown in FIG. 9, the resulting electrodes 550 may have a relatively small surface area on the outer surface of the distal portion 524 of the resulting apparatus 510. For example, the resulting electrodes 550 may extend not more than twenty percent (20%) or not more than ten percent (10%) around the circumference of the distal portion 524, which may minimize impact of the electrodes 550 on the bending properties of the distal portion 524. Alternatively, ring, coil, or other annular electrodes may be placed around the apparatus 510, e.g., over respective coils 556. The electrodes may be electrically coupled to the coils 556, e.g., by soldering, using conductive adhesive, and the like. In a further alternative, the coils 554 may provide sufficient inductive properties that no additional electrode components may be needed.

In alternative embodiments, the coil 554 may be formed after applying the jacket material or the electrode material 556 may be bonded to the coil 554 or wire termination before applying the jacket material. For example, in some embodiments, the electrodes may not need to contact tissue or fluids within the patient's body and so may remain within the outer jacket.

Optionally, other components may be added to the individual tubular devices, as desired for the particular application. For example, for a steerable catheter, a steering element 530 may be inserted through the auxiliary lumen created when the auxiliary mandrel 2b is removed. In an alternative embodiment, the auxiliary mandrel 2b may remain within the tubular device to provide the steering element, e.g., if the friction between the outer surface of the auxiliary mandrel 2b and the liner or other material defining the auxiliary lumen are relatively low. A tip or other component (not shown) may be attached to a distal end of the tubular device, e.g., after attaching one end of the steering element 530 to the tip. The other end of the steering element 530 may be coupled to an actuator of a handle attached to a proximal end of the tubular device (not shown), e.g., similar to embodiments described elsewhere herein.

The resulting apparatus 510 may be used for a variety of applications. For example, the apparatus 510 may be a guide sheath that may be used as part of an impedance and/or magnetic/inductance-based position sensing system to assist with locating one or more secondary devices, such as an ablation catheter (not shown), within a patient's body. The electrodes may be positioned at predetermined locations in order to define the curve of a deflectable distal segment, e.g. 2, 3, or more electrodes may be placed at predetermined locations along a known path length such that their relative position to one another may be used to define the arc of a deflected segment as further described below. Additionally or alternatively one or more proximal electrodes may be included, e.g. to serve as a central terminal, e.g. when positioned in the inferior vena cava or other central vessel or location within the body. Moreover, electrodes may be used for sensing electrograms, providing signals to determine position and/or for energy delivery. The system may include a controller and/or other sensor or processor (not shown) coupled to the electrodes 550 via the wires 552 (and a connector and/or cables, not shown) on the proximal end of the apparatus 510. In addition, the system may include an external detector (also not shown) also coupled to the controller, which may be positioned adjacent and external to the patient's body to activate and/or detect the electrodes 550. Thus, the system may use the electrodes 550 to "sense" the position and/or orientation of the distal portion 524 within a patient's body. Alternatively, the apparatus 510 may be an ablation catheter that uses the electrodes 550 for mapping and/or for delivering electrical energy to tissue.

With additional reference to FIG. 9, the electrodes 550 may be spaced in a desired arrangement based on the settings of the controller and/or other equipment (not shown) coupled to the electrodes 550 (e.g., via a connector on the proximal end of the apparatus 510, as described elsewhere herein). In an exemplary embodiment, the first electrode 550a may be located at the beginning of the steerable distal portion 524, the third electrode 550c may be located at the end of the steerable portion 524, and the second electrode 550b may be located half way along the steerable portion 524. When the distal portion is deflected within a patient's body, the controller or processor may interpolate the shape of the resulting deflection curve based on the positions of the electrodes, which can be used to determine the shape and location of the distal portion 524. Given that the electrodes 550 are intended simply for impedance-based sensing, the electrodes may be relatively small and can be positioned simply on one side of the distal portion 524, e.g., compared to ablation electrodes.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A tubular device for a catheter or sheath, the tubular device comprising a proximal end and a distal end sized for introduction into a patient's body, the tubular device comprising:
   a primary lumen extending between the proximal and distal ends;
   one or more elongate conducting elements extending at least partially between the proximal and distal ends adjacent the primary lumen;
   a plurality of reinforcement members braided together around the primary lumen such that the reinforcement members pass over and under one another according to a predetermined arrangement, the reinforcement members comprising windings extending helically around the primary lumen between the proximal and distal ends, at least some of the windings passing between the primary lumen and the one or more conducting elements and at least some of the windings surrounding both the primary lumen and the one or more conducting elements;
   one or more layers comprising an outer jacket surrounding the plurality of reinforcement members; and
   one or more sensing elements on a distal portion of the tubular device electrically coupled to the one or more conducting elements,
   wherein the one or more conducting elements transition to the primary lumen in an intermediate or proximal portion of the tubular device.

2. The tubular device of claim 1, wherein the one or more conducting elements comprise a plurality of wires.

3. The tubular device of claim 2, wherein the plurality of wires are electrically insulated.

4. The tubular device of claim 2, wherein the one or more sensing elements comprise a plurality of electrodes spaced apart from one another on the distal portion, wherein a first electrode of the plurality of electrodes is coupled to a first wire of the plurality of wires, and wherein a second electrode of the plurality of electrodes is coupled to a second wire of the plurality of wires.

5. The tubular device of claim 1, wherein the one or more conducting elements are embedded directly in the one or more layers.

6. The tubular device of claim 1, wherein the one or more conducting elements are disposed within a wire lumen extending at least partially between the proximal and distal ends.

7. The tubular device of claim 1, wherein the one or more conducting elements extend substantially parallel to a longitudinal axis of the tubular device at least partially between the proximal and distal ends.

8. The tubular device of claim 1, wherein the one or more conducting elements extend along a curvilinear path at least partially between the proximal and distal ends.

9. The tubular device of claim 8, wherein the curvilinear path is generally sinusoidal.

10. The tubular device of claim 1, wherein the one or more conducting elements extend helically around the primary lumen at least partially between the proximal and distal ends.

11. The tubular device of claim 1, wherein the one or more sensing elements comprise one or more electrodes mounted on the distal portion.

12. A tubular device for a catheter or sheath, the tubular device comprising a proximal end and a distal end sized for introduction into a patient's body, the tubular device comprising:
   a primary lumen extending between the proximal and distal ends;
   one or more elongate conducting elements extending at least partially between the proximal and distal ends adjacent the primary lumen;
   a plurality of reinforcement members braided together around the primary lumen such that the reinforcement members pass over and under one another according to a predetermined arrangement, the reinforcement members comprising windings extending helically around the primary lumen between the proximal and distal ends, at least some of the windings passing between the primary lumen and the one or more conducting elements and at least some of the windings surrounding both the primary lumen and the one or more conducting elements;
   one or more layers comprising an outer jacket surrounding the plurality of reinforcement members; and
   one or more sensing elements on a distal portion of the tubular device electrically coupled to the one or more conducting elements, wherein the one or more conducting elements extend helically around the primary lumen at least partially between the proximal and distal ends proximal to the distal portion, and wherein the one or more conducting elements transition outside the reinforcement members in the distal portion, wherein the one or more conducting elements transition to the primary lumen in an intermediate or proximal portion of the tubular device.

13. The tubular device of claim 12, wherein the one or more conducting elements extend along the distal portion in a curvilinear arrangement.

14. The tubular device of claim 13, wherein the curvilinear arrangement is generally sinusoidal such that the one or more conducting elements extend along the distal portion in a sinusoidal pattern immediately adjacent one another.

15. The tubular device of claim 14, wherein the one or more conducting elements are substantially centered on a neutral axis of the distal portion.

* * * * *